United States Patent
Lee et al.

(10) Patent No.: US 9,340,807 B2
(45) Date of Patent: May 17, 2016

(54) POLYNUCLEOTIDE CONFERRING ACID TOLERANT PROPERTY TO YEAST CELL AND METHOD OF PRODUCING A PRODUCT BY USING THE YEAST CELL

(71) Applicant: Samsung Electronics Co., Ltd., Suwon-si, Gyeonggi-do (KR)

(72) Inventors: Woo Yong Lee, Hwaseong-si (KR); Chang Duk Kang, Gwacheon-si (KR); Ju Young Lee, Daegu (KR); Kwang Myung Cho, Seongnam-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/474,959

(22) Filed: Sep. 2, 2014

(65) Prior Publication Data

US 2015/0064752 A1 Mar. 5, 2015

(30) Foreign Application Priority Data

Aug. 30, 2013 (KR) .......................... 10-2013-0104056

(51) Int. Cl.
| | | |
|---|---|---|
| C12N 1/15 | (2006.01) | |
| C12P 7/40 | (2006.01) | |
| C12P 7/52 | (2006.01) | |
| C12P 7/54 | (2006.01) | |
| C12P 7/56 | (2006.01) | |
| C12N 9/10 | (2006.01) | |

(52) U.S. Cl.
CPC .................. *C12P 7/56* (2013.01); *C12N 9/1051* (2013.01); *C12P 7/40* (2013.01); *Y02P 20/52* (2015.11)

(58) Field of Classification Search
None
See application file for complete search history.

(56) References Cited

U.S. PATENT DOCUMENTS

| | | |
|---|---|---|
| 2003/0219455 A1 | 11/2003 | Cole et al. |
| 2006/0211013 A1 | 9/2006 | Fontaine et al. |
| 2007/0141687 A1 | 6/2007 | Porro et al. |
| 2009/0053782 A1* | 2/2009 | Dundon et al. ............... 435/139 |
| 2011/0021378 A1 | 1/2011 | Callewaert et al. |

OTHER PUBLICATIONS

Kohler et al., "Probiotic Interference of *Lactobacillus rhamnosus* GR-1 and Lactobacillus reuteri RC-14 with the Opportunistic Fungal Pathogen *Candida albicans*" Infectious Diseases in Obstetrics and Gynecology, doi:10.1155/2012/636474, pp. 1-15 (2012).

* cited by examiner

*Primary Examiner* — David J Steadman
(74) *Attorney, Agent, or Firm* — Leydig, Voit & Mayer, Ltd.

(57) ABSTRACT

A polypeptide conferring an acid-tolerant property on a yeast cell, a polynucleotide encoding the polypeptide, a yeast cell including an increased amount of the polypeptide, a method of producing a product by using the yeast cell, and a method of producing an acid-tolerant yeast cell are provided.

18 Claims, 7 Drawing Sheets

SEQUENCE LISTING

```
<160> NUMBER OF SEQ ID NOS: 28

<210> SEQ ID NO 1
<211> LENGTH: 542
<212> TYPE: PRT
<213> ORGANISM: Issatchenkia orientalis

<400> SEQUENCE: 1

Met Lys Phe Ser Lys Ser Leu Ala Leu Leu Ser Thr Ala Leu Phe Ser
1               5                   10                  15
```

```
Gly Val Ala Thr Ala Asn Asp Asp Phe Pro Thr Ile Asn Val Val Gly
             20                  25                  30

Asn Lys Phe Phe Tyr Ser Asn Asn Ala Ser Gln Phe Tyr Ile Lys Gly
         35                  40                  45

Val Ala Tyr Gln Gln Asn Thr Ala Gly Leu Asp Thr Asp Ala Lys Tyr
 50                  55                  60

Val Asp Pro Leu Ala Asp Glu Glu Ser Cys Lys Arg Asp Ile Pro Tyr
 65                  70                  75                  80

Leu Thr Glu Leu His Thr Asn Thr Ile Arg Val Tyr Ala Leu Asn Ala
                 85                  90                  95

Ser Ala Asn His Asp Ala Cys Met Asn Ala Leu Gln Asp Ala Gly Ile
                100                 105                 110

Tyr Val Ile Ala Asp Leu Ser Ser Pro Gly Glu Ser Ile Ile Thr Ser
             115                 120                 125

Asp Pro Glu Trp Asp Leu Glu Leu Tyr Asp Arg Tyr Thr Ser Val Ile
130                 135                 140

Asp Met Met Gln Lys Tyr Asn Asn Val Leu Gly Phe Phe Ala Gly Asn
145                 150                 155                 160

Glu Val Ile Thr Asn Ser Thr Asn Thr Asp Thr Ala Pro Phe Val Lys
                 165                 170                 175

Ala Ala Ile Arg Asp Met Lys Lys Tyr Ile Ser Asp Lys Gly Tyr Arg
             180                 185                 190

Asp Ile Pro Val Gly Tyr Ser Ala Asn Asp Asp Ser Asn Thr Arg Val
         195                 200                 205

Gln Ser Ala Asp Tyr Phe Ala Cys Gly Asp Asp Ile Lys Ala Asp
     210                 215                 220

Phe Tyr Gly Ile Asn Met Tyr Glu Trp Cys Gly Asn Ser Asn Phe Lys
225                 230                 235                 240

Glu Ser Gly Tyr Glu Ala Arg Thr Lys Glu Phe Ser Asn Leu Thr Val
             245                 250                 255

Pro Ile Phe Phe Ser Glu Tyr Gly Cys Asn Glu Val Gln Pro Arg Lys
         260                 265                 270

Phe Thr Glu Val Gly Thr Ile Tyr Ser Asp Glu Met Thr Asp Val Trp
     275                 280                 285

Ser Gly Gly Ile Val Tyr Met Tyr Phe Glu Glu Glu Asn Asn Tyr Gly
290                 295                 300

Leu Val Ser Val Glu Asp Asn Lys Val Ser Thr Met Ala Asp Phe Asn
305                 310                 315                 320

Tyr Leu Lys Ser Glu Leu Gly Ser Ile Ser Pro Thr Tyr Ala Lys Ala
             325                 330                 335

Ser Ala Ser Ala Ser Ala Lys Thr Leu Gln Cys Pro Ser Thr Asp
         340                 345                 350

Lys Asn Trp Ser Ala Ala Thr Asn Leu Pro Pro Thr Pro Asp Gln Ser
     355                 360                 365

Leu Cys Asp Cys Val Glu Ser Ser Val Glu Cys Thr Val Ser Asp Asp
     370                 375                 380

Val Asp Glu Ser Asp Tyr Ser Asp Leu Phe Gly Val Val Cys Asn Tyr
385                 390                 395                 400

Ile Ser Cys Asp Glu Ile Asn Ala Asn Gly Lys Lys Gly Thr Tyr Gly
                 405                 410                 415

Ser Tyr Ser Phe Cys Asn Pro Lys Glu Lys Leu Ala Tyr Val Leu Asn
             420                 425                 430
```

```
Lys Tyr Tyr Gln Asp Gln Asp Lys Asn Lys Ser Ala Cys Asp Phe Ser
            435                 440                 445

Gly Ser Ala Thr Ile Val Lys Ser Ser Ala Ala Ser Thr Cys Ser Ser
    450                 455                 460

Ile Leu Lys Asn Ala Ser Ala Ser Gln Thr Phe Thr Asn Ser Gly Ser
465                 470                 475                 480

Thr Ala Lys Asp Ser Ser Glu Thr Lys Thr Ser Gly Ser Ala Lys Ser
                485                 490                 495

Val Ser Ser Ile Ser Ser Thr Ser Lys Gly Ala Ala Ser Leu Lys
                500                 505                 510

Ala Pro Met His Ala Ser Ser Leu Ser Ser Met Tyr Leu Cys Thr Leu
            515                 520                 525

Ile Gly Gly Val Val Val Gly Ser Ile Ser Met Ile Leu Ile
530                 535                 540
```

<210> SEQ ID NO 2
<211> LENGTH: 1629
<212> TYPE: DNA
<213> ORGANISM: Issatchenkia orientalis

<400> SEQUENCE: 2

```
atgaagttct caaagtctct cgctttacta tctactgctc tctttagcgg agtggccact      60
gctaatgacg atttccctac catcaatgtg gttggaaaca agtttttcta ctccaacaat     120
gcctctcagt tctacatcaa gggtgttgca taccaacaaa acactgcagg cttggacaca     180
gacgcaaagt atgttgatcc attggccgac gaggaaagtt gtaaaagaga cattccatat     240
ttgaccgagc tgcacacaaa taccatcaga gtgtatgccc ttaatgccag tgccaaccac     300
gatgcatgca tgaacgccct gcaagatgct ggtatttacg tcattgcaga cttgtcatct     360
ccaggtgaat ccatcattac cagtgatcca gaatgggatc ttgaattgta tgacagatac     420
acctcggtca ttgatatgat gcagaagtac aacaatgtct gggggttctt tgccggtaac     480
gaagtcatta ctaattccac aaacaccgac actgctcctt tgtcaaggc ggcaatcaga      540
gatatgaaga gtacatctc cgataagggt tataggata ttccagttgg ttattctgcg       600
aacgatgact ctaatacgag ggtccaatct gcagattatt ttgcgtgcgg tgatgatgac     660
atcaaagccg acttttatgg tatcaacatg tacgaatggt gtggtaactc caacttcaag     720
gagtccggtt acgaagctag aactaaggaa ttttccaact taactgttcc gattttcttt     780
tctgaatatg gttgtaacga agtccaacca agaaagttca ccgaagttgg tacaatttat     840
agtgacgaaa tgactgacgt ttggtctggt ggtatcgtct acatgtattt cgaggaagaa     900
aacaactacg gtttagtttc tgttgaggat aacaaggtgt caaccatggc agatttcaat     960
tacttgaagt ctgaattagg cagcatcagc ccaacctatg caaaggcttc cgcagcttct    1020
gcatctgcta aaactttaca atgtccatct actgataaga ctggtccgc agctaccaac     1080
ttacctccaa ctccagatca atccctttgt gattgtgtcg aaagttctgt tgaatgtacc    1140
gtttctgatg atgtcgatga agtgattac agtgacctgt ttggtgtggt ttgtaactac     1200
atctcctgtg atgaaattaa cgctaatggt aagaaggta cttatggttc ttactcattc    1260
tgtaatccta aggaaaagtt ggcatatgtt ttgaacaagt actatcaaga tcaagataag    1320
aataagtccg cttgtgattt ttccggctct gctactattg tgaagtcatc tgcagcttca    1380
acttgttcgt ccatcttaaa gaatgcctct gcaagccaaa cattcactaa ctctggctcc    1440
acagctaaag attcttcaga gactaagact agtggctctg ccaagtcggt ttcttcaatc    1500
```

```
agttcaactt ccaagggtgc agctgctagc ctcaaggccc aatgcatgc ttcaagtcta    1560 tcatcaatgt acttgtgtac tttaattggt ggtgttgttg tcggctccat ctctatgatt    1620
ttgatctga                                                             1629

<210> SEQ ID NO 3
<211> LENGTH: 1925
<212> TYPE: DNA
<213> ORGANISM: Issatchenkia orientalis

<400> SEQUENCE: 3 acttttctcta agcttgctgt aattgtactt ttatagttag tctttttttt agttttaaaa      60
caccagaact tagtttcgac ggattctagc agtggtatca acgcagagta cagggaagat     120
gaagttctca aagtctctcg ctttactatc tactgctctc tttagcggag tggccactgc     180
taatgacgat ttccctacca tcaatgtggt tggaaacaag ttttttctact ccaacaatgc    240 ctctcagttc tacatcaagg gtgttgcata ccaacaaaac actgcaggct tggacacaga    300
cgcaaagtat gttgatccat ggccgacga ggaaagttgt aaaagagaca ttccatattt     360
gaccgagctg cacacaaata ccatcagagt gtatgccctt aatgccagtg ccaaccacga    420
tgcatgcatg aacgccctgc aagatgctgg tatttacgtc attgcagact tgtcatctcc    480
aggtgaatcc atcattacca gtgatccaga atgggatctt gaattgtatg acagatacac    540
ctcggtcatt gatatgatgc agaagtacaa caatgtcttg ggttcttttg ccggtaacga    600
agtcattact aattccacaa acaccgacac tgctcctttt gtcaaggcgg caatcagaga    660
tatgaagaag tacatctccg ataagggtta tagggatatt ccagttggtt attctgcgaa    720
cgatgactct aatacgaggg tccaatctgc agattatttt gcgtgcggtg atgatgacat    780
caaagccgac ttttatggta tcaacatgta cgaatggtgt ggtaactcca acttcaagga    840
gtccggttac gaagctagaa ctaaggaatt tccaacttta actgttccga ttttctttc     900 tgaatatggt tgtaacgaag tccaaccaag aaagttcacc gaagttggta caatttatag    960
tgacgaaatg actgacgttt ggtctggtgg tatcgtctac atgtatttcg aggaagaaaa   1020
caactacggt ttagttttctg ttgaggataa caaggtgtca accatggcag atttcaatta   1080
cttgaagtct gaattaggca gcatcagccc aacctatgca aaggcttccg cagcttctgc   1140
atctgctaaa actttacaat gtccatctac tgataagaac tggtccgcag ctaccaactt   1200
acctccaact ccagatcaat cccttttgtga ttgtgtcgaa agttctgttg aatgtaccgt   1260
ttctgatgat gtcgatgaaa gtgattacag tgacctgttt ggtgtggttt gtaactacat   1320
ctcctgtgat gaaattaacg ctaatggtaa gaaaggtact tatggttctt actcattctg   1380
taatcctaag gaaaagttgg catatgtttt gaacaagtac tatcaagatc aagataagaa   1440
taagtccgct tgtgattttt ccggctctgc tactattgtg aagtcatctg cagcttcaac   1500
ttgttcgtcc atcttaaaga atgcctctgc aagccaaaca ttcactaact ctggctccac   1560
agctaaagat tcttcagaga ctaagactag tggctctgcc aagtcggttt cttcaatcag   1620
ttcaacttcc aagggtgcag ctgctagcct caaggcccca atgcatgctt caagtctatc   1680
atcaatgtac ttgtgtactt taattggtgg tgttgttgtc ggctccatct ctatgatttt   1740
gatctgatca ttagatatat tattttttaca tactagtatg tacaattgtt ttcttaaaat   1800
ctttactttc ttttcccctta caaaaaaaaa aaaaaaaat ggtgtctcat cgtacctcga   1860
gtcatgtaat tagttatgtc acgcttacat tcacgccctc cccccacatc cgctttacgg   1920
aaggg                                                                 1925
```

<210> SEQ ID NO 4
<211> LENGTH: 1939
<212> TYPE: DNA
<213> ORGANISM: Issatchenkia orientalis

<400> SEQUENCE: 4

| | |
|---|---:|
| acttatttct cagcttctgt aattgtactt ttatagttag tcttttttt agttttaaaa | 60 |
| caccagaact tagtttcgac ggattctagc agtggtatca acgcagagta caggggaggt | 120 |
| tctctattga caagatgaag ttctcaaagt ctctcgcttt actatctact gctctcttta | 180 |
| gcggagtggc cactgctaat gacgatttcc ctaccatcaa tgtggttgga aacaagtttt | 240 |
| tctactccaa caatgcctct cagttctaca tcaagggtgt tgcataccaa caaaacactg | 300 |
| caggcttgga cacagacgca aagtatgttg atccattggc cgacgaggaa agttgtaaaa | 360 |
| gagacattcc atatttgacc gagctgcaca caaataccat cagagtgtat gcccttaatg | 420 |
| ccagtgccaa ccacgatgca tgcatgaatg ccctgcaaga tgctggtatt tacgtcattg | 480 |
| cagacttgtc atctccaggt gaatccatca ttaccagtga tccagaatgg gatcttgaat | 540 |
| tgtatgacag atacacctcg gtcattgata tgatgcagaa gtacaacaat gtcttggggt | 600 |
| tctttgccgg taacgaagtc attactaatt ccacaaacac cgacactgct ccttttgtca | 660 |
| aggcggcaat cagagatatg aagaagtaca ctctccgataa gggttatagg gatattccag | 720 |
| ttggttattc tgcgaacgat gactctaata cgagggtcca atctgcagat tattttgcgt | 780 |
| gcggtgatga tgacatcaaa gccgactttt atggtatcaa catgtacgaa tggtgtggta | 840 |
| actccaactt caaggagtcc ggttacgaag ctagaactaa ggaattttcc aacttaactg | 900 |
| ttccgatttt cttttctgaa tatggttgta acgaagtcca accaagaaag ttcaccgaag | 960 |
| ttggtacaat ttatagtgac gaaatgactg acgtttggtc tggtggtatc gtctacatgt | 1020 |
| atttcgagga agaaaacaac tacggtttag tttctgttga ggataacaag gtgtcaacca | 1080 |
| tggcagattt caattacttg aagtctgaat taggcagcat cagcccaacc tatgcaaagg | 1140 |
| cttccgcagc ttctgcatct gctaaaactt acaatgtcc atctactgat aagaactggt | 1200 |
| ccgcagctac caacttacct ccaactccag atcaatccct ttgtgattgt gtcgaaagtt | 1260 |
| ctgttgaatg taccgtttct gatgatgtcg atgaaagtga ttacagtgac ctgtttggtg | 1320 |
| tggtttgtaa ctacatctcc tgtgatgaaa ttaacgctaa tggtaagaaa ggtacttatg | 1380 |
| gttcttactc attctgtaat cctaaggaaa agttggcata tgttttgaac aagtactatc | 1440 |
| aagatcaaga taagaataag tccgcttgtg attttttccgg ctctgctact attgtgaagt | 1500 |
| catctgcagc ttcaacttgt tcgtccatct aaagaatgc ctctgcaagc caaacattca | 1560 |
| ctaactctgg ctccacagct aaagattctt cagagactaa gactagtggc tctgccaagt | 1620 |
| cggtttcttc aatcagttca acttccaagg gtgcagctgc tagcctcaag gccccaatgc | 1680 |
| atgcttcaag tctatcatca atgtacttgt gtactttaat tggtggtgtt gttgtcggct | 1740 |
| ccatctctat gattttgatc tgatcagtag atatattatt tttacatact agtatgtaca | 1800 |
| attgttttct taaatctttt actttctttt cccttaaaaa aaaaaaaaa aaatggtgt | 1860 |
| ctcatcgtac ctcgagtcat gtaattagtt atgtcacgct tacattcacg ccctccccc | 1920 |
| acatccgctt aaccgaagt | 1939 |

<210> SEQ ID NO 5
<211> LENGTH: 1977
<212> TYPE: DNA

<213> ORGANISM: Issatchenkia orientalis

<400> SEQUENCE: 5

```
cattttttgc ccagcgtctg taattctact tttatagtta gtcttttttt tagttttaaa      60
acaccagaac ttagtttcga cggattctag cagtggtatc aacgcagagt acaggggaca     120
gttttgcttc ttgtgtcctt ttgttctctc cccttgtagg ttctctattg acaagatgaa     180
gttctcaaag tctctcgctt tactatctac tgctctcttt agcggagtgg ccactgctaa     240
tgacgatttc cctaccatca atgtggttgg aaacaagttt ttctactcca acaatgcctc     300
tcagttctac atcaagggtg ttgcatacca acaaaacact gcaggcttgg acacagacgc     360
aaagtatgtt gatccattgg ccgacgagga agttgtaaaa agagacattc catatttgac     420
cgagctgcac acaaatacca tcagagtgta tgcccttaat gccagtgcca accacgatgc     480
atgcatgaac gccctgcaag atgctggtat ttacgtcatt gcagacttgt catctccagg     540
tgaatccatc attaccagtg atccagaatg ggatcttgaa ttgtatgaca gatacacctc     600
ggtcattgat atgatgcaga agtacaacaa tgtcttgggg ttctttgccg gtaacgaagt     660
cattactaat tccacaaaca ccgacactgc tccttttgtc aaggcggcaa tcagagatat     720
gaagaagtac atctccgata agggttatag ggatattcca gttggttatt ctgcgaacga     780
tgactctaat acgagggtcc aatctgcaga ttattttgcg tgcggtgatg atgacatcaa     840
agccgacttt tatggtatca acatgtacga atggtgtggt aactccaact tcaaggagtc     900
cggttacgaa gctagaacta aggaattttc caacttaact gttccgattt tcttttctga     960
atatggttgt aacgaagtcc aaccaagaaa gttcaccgaa gttggtacaa tttatagtga    1020
cgaaatgact gacgtttggt ctggtggtat cgtctacatg tatttcgagg aagaaaacaa    1080
ctacggttta gtttctgttg aggataacaa ggtgtcaacc atggcagatt tcaattactt    1140
gaagtctgaa ttaggcagca tcagcccaac ctatgcaaag gcttccgcag cttctgcatc    1200
tgctaaaact ttacaatgtc catctactga taagaactgg tccgcagcta ccaacttacc    1260
tccaactcca gatcaatccc tttgtgattg tgtcgaaagt tctgttgaat gtaccgtttc    1320
tgatgatgtc gatgaaagtg attacagtga cctgtttggt gtggtttgta actacatctc    1380
ctgtgatgaa attaacgcta atggtaagaa aggtacttat ggttcttact cattctgtaa    1440
tcctaaggaa aagttggcat atgttttgaa caagtactat caagatcaag ataagaataa    1500
gtccgcttgt gattttttccg gctctgctac tattgtgaag tcatctgcag cttcaacttg    1560
ttcgtccatc ttaaagaatg cctctgcaag ccaaacattc actaactctg gctccacagc    1620
taaagattct tcagagacta agactagtgg ctctgccaag tcggtttctt caatcagttc    1680
aacttccaag ggtgcagctg ctagcctcaa ggccccaatg catgcttcaa gtctatcatc    1740
aatgtacttg tgtactttaa ttggtggtgt tgttgtcggc tccatctcta tgattttgat    1800
ctgatcatta gatatattat ttttacatac tagtatgtac aattgttttc ttaaaatctt    1860
tactttcttt tcccttaaaa aaaaaaaaa aaaaatggtg tctcatcgta cctcgagtca    1920
tgtaattagt tatgtcacgc ttacatcacg ccctcccccc actccgctaa ccgaggg       1977
```

<210> SEQ ID NO 6
<211> LENGTH: 44
<212> TYPE: DNA
<213> ORGANISM: Artificial Sequence
<220> FEATURE:
<223> OTHER INFORMATION: Synthetic (XbaI primer)

<400> SEQUENCE: 6
tatactttct agctagagaa taggaacttc ggaataggaa cttc    44

<210> SEQ ID NO 7
<211> LENGTH: 44
<212> TYPE: DNA
<213> ORGANISM: Artificial Sequence
<220> FEATURE:
<223> OTHER INFORMATION: Synthetic (XbaI primer)

<400> SEQUENCE: 7
cctattctct agctagaaag tataggaact tcagagcgct tttg    44

<210> SEQ ID NO 8
<211> LENGTH: 25
<212> TYPE: DNA
<213> ORGANISM: Artificial Sequence
<220> FEATURE:
<223> OTHER INFORMATION: Synthetic (PstI primer)

<400> SEQUENCE: 8
cgtttcctgg aggttttgt tctgt    25

<210> SEQ ID NO 9
<211> LENGTH: 33
<212> TYPE: DNA
<213> ORGANISM: Artificial Sequence
<220> FEATURE:
<223> OTHER INFORMATION: Synthetic (PstI primer)

<400> SEQUENCE: 9
caaaaacctc caggaaacga agataaatca tgt    33

<210> SEQ ID NO 10
<211> LENGTH: 48
<212> TYPE: DNA
<213> ORGANISM: Artificial Sequence
<220> FEATURE:
<223> OTHER INFORMATION: Synthetic (bla primer)

<400> SEQUENCE: 10
tattgaaaaa ggaagagtat gattgaacaa gatggattgc acgcaggt    48

<210> SEQ ID NO 11
<211> LENGTH: 48
<212> TYPE: DNA
<213> ORGANISM: Artificial Sequence
<220> FEATURE:
<223> OTHER INFORMATION: Synthetic (bla primer)

<400> SEQUENCE: 11
agtaaacttg gtctgacatc agaagaactc gtcaagaagg cgatagaa    48

<210> SEQ ID NO 12
<211> LENGTH: 29
<212> TYPE: DNA
<213> ORGANISM: Artificial Sequence
<220> FEATURE:
<223> OTHER INFORMATION: Synthetic (neo primer)

<400> SEQUENCE: 12
actcttcctt tttcaatatt attgaagca    29

<210> SEQ ID NO 13
<211> LENGTH: 24
<212> TYPE: DNA

<213> ORGANISM: Artificial Sequence
<220> FEATURE:
<223> OTHER INFORMATION: Synthetic (neo primer)

<400> SEQUENCE: 13
ctgtcagacc aagtttactc atat                                              24

<210> SEQ ID NO 14
<211> LENGTH: 24
<212> TYPE: DNA
<213> ORGANISM: Artificial Sequence
<220> FEATURE:
<223> OTHER INFORMATION: Synthetic (GPDpro-F primer)

<400> SEQUENCE: 14
cggtaggtat tgattgtaat tctg                                              24

<210> SEQ ID NO 15
<211> LENGTH: 21
<212> TYPE: DNA
<213> ORGANISM: Artificial Sequence
<220> FEATURE:
<223> OTHER INFORMATION: Synthetic (GPDpro-R3 primer)

<400> SEQUENCE: 15
agacttcagg ttgtctaact c                                                 21

<210> SEQ ID NO 16
<211> LENGTH: 56
<212> TYPE: DNA
<213> ORGANISM: Artificial Sequence
<220> FEATURE:
<223> OTHER INFORMATION: Synthetic (IoGAS1 gene amplification primer)

<400> SEQUENCE: 16
gtttcgacgg attctagaaa acaatgaagt tctcaaagtc tctcgcttta ctatct          56

<210> SEQ ID NO 17
<211> LENGTH: 45
<212> TYPE: DNA
<213> ORGANISM: Artificial Sequence
<220> FEATURE:
<223> OTHER INFORMATION: Synthetic (IoGAS1 gene amplification primer)

<400> SEQUENCE: 17
ctaattacat gactcgagtc agatcaaaat catagagatg gagcc                       45

<210> SEQ ID NO 18
<211> LENGTH: 8109
<212> TYPE: DNA
<213> ORGANISM: Artificial Sequence
<220> FEATURE:
<223> OTHER INFORMATION: Synthetic (pRS426GPD-KanPX IoGAS1 vector)

<400> SEQUENCE: 18
gacgaaaggg cctcgtgata cgcctatttt tataggttaa tgtcatgata ataatggttt       60
cttagtatga tccaatatca aaggaaatga tagcattgaa ggatgagact aatccaattg      120
aggagtggca gcatatagaa cagctaaagg gtagtgctga aggaagcata cgatacccg      180 catggaatgg gataatatca caggaggtac tagactacct ttcatcctac ataaatagac      240
gcatataagt acgcatttaa gcataaacac gcactatgcc gttcttctca tgtatatata      300
tatacaggca acacgcagat ataggtgcga cgtgaacagt gagctgtatg tgcgcagctc      360
gcgttgcatt ttcggaagcg ctcgttttcg gaaacgcttt gaagttccta ttccgaagtt      420

```
cctattctct agctagaaag tataggaact tcagagcgct tttgaaaacc aaaagcgctc    480
tgaagacgca ctttcaaaaa accaaaaacg caccggactg taacgagcta ctaaaatatt    540
gcgaataccg cttccacaaa cattgctcaa aagtatctct ttgctatata tctctgtgct    600
atatccctat ataacctacc catccacctt tcgctccttg aacttgcatc taaactcgac    660
ctctacattt tttatgttta tctctagtat tactctttag acaaaaaaat tgtagtaaga    720
actattcata gagtgaatcg aaaacaatac gaaaatgtaa acatttccta tacgtagtat    780
atagagacaa aatagaagaa accgttcata attttctgac caatgaagaa tcatcaacgc    840
tatcactttc tgttcacaaa gtatgcgcaa tccacatcgg tatagaatat aatcggggat    900
gcctttatct tgaaaaaatg cacccgcagc ttcgctagta atcagtaaac gcgggaagtg    960
gagtcaggct ttttttatgg aagagaaaat agacaccaaa gtagccttct tctaaccttg   1020
acggacctac agtgcaaaaa gttatcaaga gactgcatta tagagcgcac aaaggagaaa   1080
aaaagtaatc taagatgctt tgttagaaaa atagcgctct cgggatgcat ttttgtagaa   1140 caaaaagaa gtatagattc tttgttggta aaatagcgct ctcgcgttgc atttctgttc    1200
tgtaaaaatg cagctcagat tctttgtttg aaaaattagc gctctcgcgt tgcattttg    1260 ttttacaaaa atgaagcaca gattcttcgt tggtaaaata gcgctttcgc gttgcatttc   1320
tgttctgtaa aaatgcagct cagattcttt gtttgaaaaa ttagcgctct cgcgttgcat   1380
ttttgttcta caaaatgaag cacagatgct tcgttcaggt ggcacttttc ggggaaatgt   1440
gcgcggaacc cctatttgtt tattttttcta aatacattca aatatgtatc cgctcatgag   1500
acaataaccc tgataaatgc ttcaataata ttgaaaaagg aagagtatga ttgaacaaga   1560
tggattgcac gcaggttctc cggccgcttg ggtggagagg ctattcggct atgactgggc   1620
acaacagaca atcggctgct ctgatgccgc cgtgttccgg ctgtcagcgc aggggcgccc   1680
ggttcttttt gtcaagaccg acctgtccgg tgccctgaat gaactgcaag acgaggcagc   1740
gcggctatcg tggctggcca cgacgggcgt tccttgcgca gctgtgctcg acgttgtcac   1800
tgaagcggga agggactggc tgctattggg cgaagtgccg gggcaggatc tcctgtcatc   1860
tcaccttgct cctgccgaga aagtatccat catggctgat gcaatgcggc ggctgcatac   1920
gcttgatccg gctacctgcc cattcgacca ccaagcgaaa catcgcatcg agcgagcacg   1980
tactcggatg aagccggtc ttgtcgatca ggatgatctg gacgaagagc atcagggct    2040 cgcgccagcc gaactgttcg ccaggctcaa ggcgagcatg cccgacggcg aggatctcgt   2100
cgtgacccat ggcgatgcct gcttgccgaa tatcatggtg gaaaatggcc gcttttctgg   2160
attcatcgac tgtggccggc tgggtgtggc ggaccgctat caggacatag cgttggctac   2220
ccgtgatatt gctgaagagc ttggcggcga atgggctgac cgcttcctcg tgctttacgg   2280
tatcgccgct cccgattcgc agcgcatcgc cttctatcgc cttcttgacg agttcttctg   2340
atgtcagacc aagtttactc atatatactt tagattgatt taaaacttca ttttttaattt   2400 aaaaggatct aggtgaagat cctttttgat aatctcatga ccaaaatccc ttaacgtgag   2460
ttttcgttcc actgagcgtc agaccccgta gaaaagatca aggatcttc ttgagatcct    2520 ttttttctgc gcgtaatctg ctgcttgcaa acaaaaaaac caccgctacc agcggtggtt   2580
tgtttgccgg atcaagagct accaactctt tttccgaagg taactggctt cagcagagcg   2640
cagataccaa atactgttct tctagtgtag ccgtagttag gccaccactt caagaactct   2700
gtagcaccgc ctacatacct cgctctgcta atcctgttac cagtggctgc tgccagtggc   2760
```

```
gataagtcgt gtcttaccgg gttggactca agacgatagt taccggataa ggcgcagcgg    2820
tcgggctgaa cggggggttc gtgcacacag cccagcttgg agcgaacgac ctacaccgaa    2880
ctgagatacc tacagcgtga gctatgagaa agcgccacgc ttcccgaagg gagaaaggcg    2940
gacaggtatc cggtaagcgg cagggtcgga acaggagagc gcacgaggga gcttccaggg    3000
ggaaacgcct ggtatcttta tagtcctgtc gggtttcgcc acctctgact tgagcgtcga    3060
tttttgtgat gctcgtcagg ggggcggagc ctatggaaaa acgccagcaa cgcggccttt    3120
ttacggttcc tggccttttg ctggcctttt gctcacatgt tctttcctgc gttatcccct    3180
gattctgtgg ataaccgtat taccgccttt gagtgagctg ataccgctcg ccgcagccga    3240
acgaccgagc gcagcgagtc agtgagcgag gaagcggaag agcgcccaat acgcaaaccg    3300
cctctccccg cgcgttggcc gattcattaa tgcagctggc acgacaggtt cccgactgg    3360 aaagcgggca gtgagcgcaa cgcaattaat gtgagttagc tcactcatta ggcaccccag    3420
gctttacact ttatgcttcc ggctcgtatg ttgtgtggaa ttgtgagcgg ataacaattt    3480
cacacaggaa acagctatga ccatgattac gccaagcgcg caattaaccc tcactaaagg    3540
gaacaaaagc tggagctcag tttatcatta tcaatactcg ccatttcaaa gaatacgtaa    3600
ataattaata gtagtgattt tcctaacttt atttagtcaa aaaattagcc ttttaattct    3660
gctgtaaccc gtacatgccc aaaataggg gcgggttaca cagaatatat aacatcgtag    3720
gtgtctgggt gaacagttta ttcctggcat ccactaaata taatggagcc gcttttaa    3780 gctggcatcc agaaaaaaaa agaatcccag caccaaaata ttgttttctt caccaaccat    3840
cagttcatag gtccattctc ttagcgcaac tacagagaac aggggcacaa acaggcaaaa    3900
aacgggcaca acctcaatgg agtgatgcaa cctgcctgga gtaaatgatg acacaaggca    3960
attgacccac gcatgtatct atctcatttt cttacacctt ctattacctt ctgctctctc    4020
tgatttggaa aaagctgaaa aaaaaggttg aaaccagttc cctgaaatta ttccccctact    4080 tgactaataa gtatataaag acggtaggta ttgattgtaa ttctgtaaat ctatttctta    4140
aacttcttaa attctacttt tatagttagt cttttttta gttttaaaac accagaactt    4200
agtttcgacg gattctagaa acaatgaag ttctcaaagt ctctcgcttt actatctact    4260 gctctctta gcggagtggc cactgctaat gacgatttcc ctaccatcaa tgtggttgga    4320
aacaagtttt tctactccaa caatgcctct cagttctaca tcaagggtgt tgcataccaa    4380
caaaacactg caggcttgga cacagacgca aagtatgttg atccattggc cgacgaggaa    4440
agttgtaaaa gagacattcc atattttgacc gagctgcaca caaataccat cagagtgtat    4500
gcccttaatg ccagtgccaa ccacgatgca tgcatgaacg ccctgcaaga tgctggtatt    4560
tacgtcattg cagacttgtc atctccaggt gaatccatca ttaccagtga tccagaatgg    4620
gatcttgaat tgtatgacag atacacctcg gtcattgata tgatgcagaa gtacaacaat    4680
gtcttggggt tctttgccgg taacgaagtc attactaatt ccacaaacac cgacactgct    4740 cctttttgtca aggcggcaat cagagatatg aagaagtaca tctccgataa gggttatagg    4800
gatattccag ttggttattc tgcgaacgat gactctaata cgagggtcca atctgcagat    4860
tattttgcgt gcggtgatga tgacatcaaa gccgactttt atggtatcaa catgtacgaa    4920
tggtgtggta actccaactt caaggagtcc ggttacgaag ctagaactaa ggaattttcc    4980
aacttaactg ttccgatttt cttttctgaa tatggttgta acgaagtcca accaagaaag    5040
ttcaccgaag ttggtacaat ttatagtgac gaaatgactg acgttggtc tggtggtatc    5100 gtctacatgt atttcgagga agaaaacaac tacggtttag tttctgttga ggataacaag    5160
```

```
gtgtcaacca tggcagattt caattacttg aagtctgaat taggcagcat cagcccaacc   5220
tatgcaaagg cttccgcagc ttctgcatct gctaaaactt tacaatgtcc atctactgat   5280
aagaactggt ccgcagctac caacttacct ccaactccag atcaatccct tgtgattgt    5340 gtcgaaagtt ctgttgaatg taccgtttct gatgatgtcg atgaaagtga ttacagtgac   5400
ctgtttggtg tggtttgtaa ctacatctcc tgtgatgaaa ttaacgctaa tggtaagaaa   5460
ggtacttatg gttcttactc attctgtaat cctaaggaaa agttggcata tgttttgaac   5520
aagtactatc aagatcaaga taagaataag tccgcttgtg atttttccgg ctctgctact   5580
attgtgaagt catctgcagc ttcaacttgt tcgtccatct taaagaatgc ctctgcaagc   5640
caaacattca ctaactctgg ctccacagct aaagattctt cagagactaa gactagtggc   5700
tctgccaagt cggtttcttc aatcagttca acttccaagg gtgcagctgc tagcctcaag   5760
gccccaatgc atgcttcaag tctatcatca atgtacttgt gtactttaat tggtggtgtt   5820
gttgtcggct ccatctctat gattttgatc tgactcgagt catgtaatta gttatgtcac   5880
gcttacattc acgccctccc cccacatccg ctctaaccga aaaggaagga gttagacaac   5940
ctgaagtcta ggtccctatt tattttttta tagttatgtt agtattaaga acgttattta   6000
tatttcaaat ttttctttt tttctgtaca gacgcgtgta cgcatgtaac attatactga    6060
aaaccttgct tgagaaggtt ttgggacgct cgaaggcttt aatttgcggc cggtacccaa   6120
ttcgccctat agtgagtcgt attacgcgcg ctcactggcc gtcgttttac aacgtcgtga   6180
ctggaaaaac cctggcgtta cccaacttaa tcgccttgca gcacatcccc ctttcgccag   6240
ctggcgtaat agcgaagagg cccgcaccga tcgcccttcc caacagttgc gcagcctgaa   6300
tggcgaatgg acgcgccctg tagcggcgca ttaagcgcgg cgggtgtggt ggttacgcgc   6360
agcgtgaccg ctacacttgc cagcgcccta gcgcccgctc ctttcgcttt cttcccttcc   6420
tttctcgcca cgttcgccgg ctttccccgt caagctctaa atcggggggct ccctttaggg   6480 ttccgattta gtgctttacg gcacctcgac cccaaaaaac ttgattaggg tgatggttca   6540
cgtagtgggc catcgccctg atagacggtt tttcgccctt tgacgttgga gtccacgttc   6600
tttaatagtg gactcttgtt ccaaactgga acaacactca accctatctc ggtctattct   6660
tttgatttat aagggatttt gccgatttcg gcctattggt taaaaaatga gctgatttaa   6720
caaaaattta cgcgaattt taacaaaata ttaacgctta caatttcctg atgcggtatt    6780
ttctccttac gcatctgtgc ggtatttcac accgcatagg gtaataactg atataattaa   6840
attgaagctc taatttgtga gtttagtata catgcattta cttataatac agttttttag   6900
ttttgctggc cgcatcttct caaatatgct tcccagcctg cttttctgta acgttcaccc   6960
tctaccttag catcccttcc ctttgcaaat agtcctcttc caacaataat aatgtcagat   7020
cctgtagaga ccacatcatc cacggttcta tactgttgac ccaatgcgtc tcccttgtca   7080
tctaaaccca caccgggtgt cataatcaac caatcgtaac cttcatctct tccacccatg   7140
tctctttgag caataaagcc gataacaaaa tctttgtcgc tcttcgcaat gtcaacagta   7200
cccttagtat attctccagt agatagggag cccttgcatg acaattctgc taacatcaaa   7260
aggcctctag gttcctttgt tacttcttct gccgcctgct tcaaaccgct aacaatacct   7320
gggcccacca caccgtgtgc attcgtaatg tctgcccatt ctgctattct gtatacaccc   7380
gcagagtact gcaatttgac tgtattacca atgtcagcaa attttctgtc ttcgaagagt   7440
aaaaaattgt acttggcgga taatgccttt agcggcttaa ctgtgccctc catggaaaaa   7500
```

```
tcagtcaaga tatccacatg tgtttttagt aaacaaattt tgggacctaa tgcttcaact    7560
aactccagta attccttggt ggtacgaaca tccaatgaag cacacaagtt tgtttgcttt    7620
tcgtgcatga tattaaatag cttggcagca acaggactag gatgagtagc agcacgttcc    7680
ttatatgtag ctttcgacat gatttatctt cgtttcctgg aggttttgt tctgtgcagt     7740 tgggttaaga atactgggca atttcatgtt tcttcaacac tacatatgcg tatatatacc    7800
aatctaagtc tgtgctcctt ccttcgttct tccttctgtt cggagattac cgaatcaaaa    7860
aaatttcaag gaaaccgaaa tcaaaaaaaa gaataaaaaa aaaatgatga attgaaaagg    7920
tggtatggtg cactctcagt acaatctgct ctgatgccgc atagttaagc cagccccgac    7980
acccgccaac acccgctgac gcgccctgac gggcttgtct gctcccggca tccgcttaca    8040
gacaagctgt gaccgtctcc gggagctgca tgtgtcagag gttttcaccg tcatcaccga    8100
aacgcgcga                                                            8109
```

<210> SEQ ID NO 19
<211> LENGTH: 324
<212> TYPE: PRT
<213> ORGANISM: Sordaria macrospora

<400> SEQUENCE: 19

```
Met Ser Val Pro Ser Thr Glu Ile Ser Ser His Ala Lys Ser Ile Lys
1               5                   10                  15

Val Val Ile Val Gly Ala Gly Ser Val Gly Val Thr Thr Ala Tyr Ala
            20                  25                  30

Leu Leu Leu Ser His Leu Ala Pro Glu Ile Val Leu Ile Asp Ile Asp
        35                  40                  45

Lys Asn Arg Ala Leu Gly Glu Ala Met Asp Leu Ser His Ala Ala His
    50                  55                  60

Tyr Ala His Ala Lys Val Ser Val Gly Asn Tyr Glu Asp Cys Ala Gly
65                  70                  75                  80

Ala Thr Ala Val Ile Ile Thr Ala Gly Val Asn Gln Lys Pro Gly Gln
                85                  90                  95

Thr Arg Met Asp Leu Val Lys Thr Asn Phe Gly Leu Phe Glu Lys Ile
            100                 105                 110

Val Pro Gln Ile Ala Lys His Ala Pro Asn Thr Ile Leu Ile Val Ala
        115                 120                 125

Thr Asn Pro Cys Asp Val Leu Thr Lys Ala Ala Gln Glu Leu Ser Gly
    130                 135                 140

Phe Pro Val Gln Arg Val Ile Gly Ser Gly Thr Ala Met Asp Thr Thr
145                 150                 155                 160

Arg Phe Arg His Glu Leu Gly Lys His Tyr Gly Val Asn Pro Arg Asn
                165                 170                 175

Val His Ala Val Ile Val Gly Glu His Gly Asp Ser Gln Leu Pro Val
            180                 185                 190

Trp Ser Leu Ala Thr Ile Ala Gly Met Arg Leu Glu Asp Tyr Cys Asn
        195                 200                 205

Gln Lys Gly Ile Ala Tyr Asp Glu Lys Ala Met Asp Ala Leu Gly Lys
    210                 215                 220

Arg Thr Arg Glu Ala Ala Tyr Glu Ile Ile Gln Arg Lys Gly Lys Thr
225                 230                 235                 240

Asn Tyr Gly Val Ala Ser Val Leu Val Ser Ile Leu Glu Pro Ile Ile
                245                 250                 255

Thr Asn Ala Asp Gln Leu Val Thr Val Ser Arg Val Gly Asn Tyr Ala
```

```
            260                 265                 270
Gly Val Glu Gly Val Ala Leu Ser Met Pro Cys Lys Leu Asn Ser Leu
            275                 280                 285

Gly Ala His Gln Asp Val Glu Leu Leu Leu Asn Asp Lys Glu Lys Glu
            290                 295                 300

Ala Leu Arg Lys Ser Ala Thr Ser Ile Lys Glu Cys Phe Asp Ser Val
305                 310                 315                 320

Ala Lys Lys Glu

<210> SEQ ID NO 20
<211> LENGTH: 975
<212> TYPE: DNA
<213> ORGANISM: Sordaria macrospora

<400> SEQUENCE: 20
atgagcgttc caagcacaga gatttcatct catgccaaat ctataaaggt tgtcatcgtt      60
ggtgcgggtt cagttggtgt cacaactgct tatgccttat tgctttcgca cttagcacca     120
gagatcgttc tgatcgacat tgataaaaat agagctttag gagaggcaat ggacctgtca     180
catgcagctc attacgctca cgcaaaagtt agtgttggaa actatgagga ttgtgctggg     240
gccacagcag ttatcataac agctggtgtt aaccaaaagc cagggcaaac taggatggat     300
ttagtcaaaa caaactttgg actatttgag aagatagtgc cccaaatagc taagcacgcg     360
cctaatacta ttttaatagt cgctaccaat ccctgtgatg tcttaacaaa agcggcacag     420
gagttatcag gattccctgt acagagagtt atcggttctg aaccgctat ggatactacc     480 cgtttcagac acgaactggg caagcattat ggagtaaatc aagaaacgt acatgctgtg     540 attgtaggtg aacatggtga ttcccaacta cctgtatggt ccttagctac tattgctggt     600
atgcgtttgg aagattattg caatcaaaaa ggtatagcct acgatgaaaa agctatggat     660
gccttgggta aaagaactag ggaagcagca tacgaaatca ttcaaagaaa aggcaagacg     720
aattatggcg tggcatcggt ccttgtatct attttggaac cgattattac caatgcagac     780
caacttgtga ctgtctctag ggtgggcaat tacgccggtg tagaaggcgt ggctttaagt     840
atgccatgca aattgaacag tctaggtgcg catcaggacg ttgaattgtt gcttaacgac     900
aaggaaaaag aagccctacg taaatcagcc acgtccatta agaatgtttt tgattctgtt     960
gcaaagaagg aataa                                                      975

<210> SEQ ID NO 21
<211> LENGTH: 563
<212> TYPE: PRT
<213> ORGANISM: Saccharomyces cerevisiae

<400> SEQUENCE: 21

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
```

```
                        85                  90                  95
His Val Val Gly Val Pro Ser Ile Ser Ser Gln Ala Lys Gln Leu Leu
                100                 105                 110
Leu His His Thr Leu Gly Asn Gly Asp Phe Thr Val Phe His Arg Met
                115                 120                 125
Ser Ala Asn Ile Ser Glu Thr Thr Ala Met Ile Thr Asp Ile Ala Thr
            130                 135                 140
Ala Pro Ala Glu Ile Asp Arg Cys Ile Arg Thr Thr Tyr Val Thr Gln
145                 150                 155                 160
Arg Pro Val Tyr Leu Gly Leu Pro Ala Asn Leu Val Asp Leu Asn Val
                165                 170                 175
Pro Ala Lys Leu Leu Gln Thr Pro Ile Asp Met Ser Leu Lys Pro Asn
                180                 185                 190
Asp Ala Glu Ser Glu Lys Glu Val Ile Asp Thr Ile Leu Ala Leu Val
                195                 200                 205
Lys Asp Ala Lys Asn Pro Val Ile Leu Ala Asp Ala Cys Cys Ser Arg
210                 215                 220
His Asp Val Lys Ala Glu Thr Lys Lys Leu Ile Asp Leu Thr Gln Phe
225                 230                 235                 240
Pro Ala Phe Val Thr Pro Met Gly Lys Gly Ser Ile Asp Glu Gln His
                245                 250                 255
Pro Arg Tyr Gly Gly Val Tyr Val Gly Thr Leu Ser Lys Pro Glu Val
                260                 265                 270
Lys Glu Ala Val Glu Ser Ala Asp Leu Ile Leu Ser Val Gly Ala Leu
                275                 280                 285
Leu Ser Asp Phe Asn Thr Gly Ser Phe Ser Tyr Ser Tyr Lys Thr Lys
            290                 295                 300
Asn Ile Val Glu Phe His Ser Asp His Met Lys Ile Arg Asn Ala Thr
305                 310                 315                 320
Phe Pro Gly Val Gln Met Lys Phe Val Leu Gln Lys Leu Leu Thr Asn
                325                 330                 335
Ile Ala Asp Ala Ala Lys Gly Tyr Lys Pro Val Ala Val Pro Ala Arg
                340                 345                 350
Thr Pro Ala Asn Ala Ala Val Pro Ala Ser Thr Pro Leu Lys Gln Glu
            355                 360                 365
Trp Met Trp Asn Gln Leu Gly Asn Phe Leu Gln Glu Gly Asp Val Val
            370                 375                 380
Ile Ala Glu Thr Gly Thr Ser Ala Phe Gly Ile Asn Gln Thr Thr Phe
385                 390                 395                 400
Pro Asn Asn Thr Tyr Gly Ile Ser Gln Val Leu Trp Gly Ser Ile Gly
                405                 410                 415
Phe Thr Thr Gly Ala Thr Leu Gly Ala Ala Phe Ala Ala Glu Glu Ile
                420                 425                 430
Asp Pro Lys Lys Arg Val Ile Leu Phe Ile Gly Asp Gly Ser Leu Gln
                435                 440                 445
Leu Thr Val Gln Glu Ile Ser Thr Met Ile Arg Trp Gly Leu Lys Pro
            450                 455                 460
Tyr Leu Phe Val Leu Asn Asn Asp Gly Tyr Thr Ile Glu Lys Leu Ile
465                 470                 475                 480
His Gly Pro Lys Ala Gln Tyr Asn Glu Ile Gln Gly Trp Asp His Leu
                485                 490                 495
Ser Leu Leu Pro Thr Phe Gly Ala Lys Asp Tyr Glu Thr His Arg Val
                500                 505                 510
```

Ala Thr Thr Gly Glu Trp Asp Lys Leu Thr Gln Asp Lys Ser Phe Asn
        515                 520                 525

Asp Asn Ser Lys Ile Arg Met Ile Glu Val Met Leu Pro Val Phe Asp
        530                 535                 540

Ala Pro Gln Asn Leu Val Glu Gln Ala Lys Leu Thr Ala Ala Thr Asn
545                 550                 555                 560

Ala Lys Gln

<210> SEQ ID NO 22
<211> LENGTH: 1692
<212> TYPE: DNA
<213> ORGANISM: Saccharomyces cerevisiae

<400> SEQUENCE: 22

```
atgtctgaaa ttactttggg taaatatttg ttcgaaagat taaagcaagt caacgttaac      60
accgttttcg gtttgccagg tgacttcaac ttgtccttgt tggacaagat ctacgaagtt     120
gaaggtatga gatgggctgg taacgccaac gaattgaacg ctgcttacgc cgctgatggt     180
tacgctcgta tcaagggtat gtcttgtatc atcaccacct tcggtgtcgg tgaattgtct     240
gctttgaacg gtattgccgg ttcttacgct gaacacgtcg gtgttttgca cgttgttggt     300
gtcccatcca tctcttctca agctaagcaa ttgttgttgc accacacctt gggtaacggt     360
gacttcactg ttttccacag aatgtctgcc aacatttctg aaaccactgc tatgatcact     420
gacattgcta ccgccccagc tgaaattgac agatgtatca gaaccactta cgtcacccaa     480
agaccagtct acttaggttt gccagctaac ttggtcgact gaacgtccc agctaagttg     540
ttgcaaactc caattgacat gtctttgaag ccaaacgatg ctgaatccga aaaggaagtc     600
attgacacca tcttggcttt ggtcaaggat gctaagaacc cagttatctt ggctgatgct     660
tgttgttcca gacacgacgt caaggctgaa actaagaagt tgattgactt gactcaattc     720
ccagctttcg tcaccccaat gggtaagggt tccattgacg aacaacaccc aagatacggt     780
ggtgtttacg tcggtacctt gtccaagcca gaagttaagg aagccgttga atctgctgac     840
ttgattttgt ctgtcggtgc tttgttgtct gatttcaaca ccggttcttt ctcttactct     900
tacaagacca gaacattgt cgaattccac tccgaccaca tgaagatcag aaacgccact     960
ttcccaggtg tccaaatgaa attcgttttg caaaagttgt tgaccaatat tgctgacgcc    1020
gctaagggtt acaagccagt tgctgtccca gctagaactc cagctaacgc tgctgtccca    1080
gcttctaccc cattgaagca gaatggatg tggaaccaat tgggtaactt cttgcaagaa    1140
ggtgatgttg tcattgctga accggtacc tccgctttcg gtatcaacca aaccactttc    1200
ccaaacaaca cctacggtat ctctcaagtc ttatggggtt ccattggttt caccactggt    1260
gctaccttgg gtgctgcttt cgctgctgaa gaaattgatc aaagaagag agttatctta    1320
ttcattggtg acggttcttt gcaattgact gttcaagaaa tctccaccat gatcagatgg    1380
ggcttgaagc catacttgtt cgtcttgaac aacgatggtt acaccattga aaagttgatt    1440
cacggtccaa aggctcaata aacgaaatt caaggttggg accacctatc cttgttgcca    1500
actttcggtg ctaaggacta cgaaacccac agagtcgcta ccaccggtga atgggacaag    1560
ttgacccaag acaagtcttt caacgacaac tctaagatca gaatgattga ggttatgttg    1620
ccagtcttcg atgctccaca aaacttggtt gaacaagcta agttgactgc tgctaccaac    1680
gctaagcaat aa                                                         1692
```

<210> SEQ ID NO 23
<211> LENGTH: 591
<212> TYPE: PRT
<213> ORGANISM: Saccharomyces cerevisiae

<400> SEQUENCE: 23

```
Met Leu Lys Tyr Lys Pro Leu Leu Lys Ile Ser Lys Asn Cys Glu Ala
  1               5                  10                  15

Ala Ile Leu Arg Ala Ser Lys Thr Arg Leu Asn Thr Ile Arg Ala Tyr
             20                  25                  30

Gly Ser Thr Val Pro Lys Ser Lys Ser Phe Glu Gln Asp Ser Arg Lys
         35                  40                  45

Arg Thr Gln Ser Trp Thr Ala Leu Arg Val Gly Ala Ile Leu Ala Ala
     50                  55                  60

Thr Ser Ser Val Ala Tyr Leu Asn Trp His Asn Gly Gln Ile Asp Asn
 65                  70                  75                  80

Glu Pro Lys Leu Asp Met Asn Lys Gln Lys Ile Ser Pro Ala Glu Val
                 85                  90                  95

Ala Lys His Asn Lys Pro Asp Asp Cys Trp Val Ile Asn Gly Tyr
            100                 105                 110

Val Tyr Asp Leu Thr Arg Phe Leu Pro Asn His Pro Gly Gly Gln Asp
        115                 120                 125

Val Ile Lys Phe Asn Ala Gly Lys Asp Val Thr Ala Ile Phe Glu Pro
    130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                165                 170                 175

Tyr Ala Pro Gly Glu Thr Lys Glu Asp Ile Ala Arg Lys Glu Gln Leu
            180                 185                 190

Lys Ser Leu Leu Pro Pro Leu Asp Asn Ile Ile Asn Leu Tyr Asp Phe
        195                 200                 205

Glu Tyr Leu Ala Ser Gln Thr Leu Thr Lys Gln Ala Trp Ala Tyr Tyr
    210                 215                 220

Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
                245                 250                 255

Val Asp Ile Ser Thr Asp Met Leu Gly Ser His Val Asp Val Pro Phe
            260                 265                 270

Tyr Val Ser Ala Thr Ala Leu Cys Lys Leu Gly Asn Pro Leu Glu Gly
        275                 280                 285

Glu Lys Asp Val Ala Arg Gly Cys Gly Gln Gly Val Thr Lys Val Pro
    290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
                325                 330                 335

Ser Asp Arg Lys Ile Thr Asp Asp Leu Val Lys Asn Val Glu Lys Leu
            340                 345                 350

Gly Val Lys Ala Leu Phe Val Thr Val Asp Ala Pro Ser Leu Gly Gln
        355                 360                 365

Arg Glu Lys Asp Met Lys Leu Lys Phe Ser Asn Thr Lys Ala Gly Pro
    370                 375                 380
```

```
Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
            405                 410                 415

Glu Leu Lys Lys Lys Thr Lys Leu Pro Ile Val Ile Lys Gly Val Gln
            420                 425                 430

Arg Thr Glu Asp Val Ile Lys Ala Ala Glu Ile Gly Val Ser Gly Val
            435                 440                 445

Val Leu Ser Asn His Gly Gly Arg Gln Leu Asp Phe Ser Arg Ala Pro
    450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
            485                 490                 495

Asp Val Leu Lys Ala Leu Cys Leu Gly Ala Lys Gly Val Gly Leu Gly
            500                 505                 510

Arg Pro Phe Leu Tyr Ala Asn Ser Cys Tyr Gly Arg Asn Gly Val Glu
    515                 520                 525

Lys Ala Ile Glu Ile Leu Arg Asp Glu Ile Glu Met Ser Met Arg Leu
    530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
            565                 570                 575

Asn Glu Val Tyr Glu Gly Pro Thr Leu Thr Glu Phe Glu Asp Ala
    580                 585                 590
```

<210> SEQ ID NO 24
<211> LENGTH: 1776
<212> TYPE: DNA
<213> ORGANISM: Saccharomyces cerevisiae

<400> SEQUENCE: 24

```
atgctaaaat acaaaccttt actaaaaatc tcgaagaact gtgaggctgc tatcctcaga    60
gcgtctaaga ctagattgaa cacaatccgc gcgtacggtt ctaccgttcc aaaatccaag   120
tcgttcgaac aagactcaag aaaacgcaca cagtcatgga ctgccttgag agtcggtgca   180
attctagccg ctactagttc cgtggcgtat ctaaactggc ataatggcca aatagacaac   240
gagccgaaac tggatatgaa taaacaaaag atttcgcccg ctgaagttgc aagcataac    300
aagcccgatg attgttgggt gtgatcaat ggttacgtat acgacttaac gcgattccta   360
ccaaatcatc caggtgggca ggatgttatc aagtttaacg ccgggaaaga tgtcactgct   420
atttttgaac cactacatgc tcctaatgtc atcgataagt atatagctcc cgagaaaaaa   480
ttgggtcccc ttcaaggatc catgcctcct gaacttgtct gtcctcctta tgctcctggt   540
gaaactaagg aagatatcgc tagaaaagaa caactaaaat cgctgctacc tcctctagat   600
aatattatta accttacga ctttgaatac ttggcctctc aaactttgac taaacaagcg   660
tgggcctact attcctccgg tgctaacgac gaagttactc acagagaaaa ccataatgct   720
tatcatagga ttttttcaa accaaagatc cttgtagatg tacgcaaagt agacatttca   780
actgacatgt tgggttctca tgtggatgtt cccttctacg tgtctgctac agctttgtgt   840
aaactgggaa acccctaga aggtgaaaaa gatgtcgcca gaggttgtgg ccaaggtgtg   900
acaaaagtcc cacaaatgat atctactttg gcttcatgtt cccctgagga aattattgaa   960
```

```
gcagcaccct ctgataaaca aattcaatgg taccaactat atgttaactc tgatagaaag    1020
atcactgatg atttggttaa aaatgtagaa aagctgggtg taaaggcatt atttgtcact    1080
gtggatgctc caagtttagg tcaaagagaa aaagatatga agctgaaatt ttccaataca    1140
aaggctggtc caaaagcgat gaagaaaact aatgtagaag aatctcaagg tgcttcgaga    1200
gcgttatcaa agtttattga cccctctttg acttggaaag atatagaaga gttgaagaaa    1260
aagacaaaac tacctattgt tatcaaaggt gttcaacgta ccgaagatgt tatcaaagca    1320
gcagaaatcg gtgtaagtgg ggtggttcta tccaatcatg gtggtagaca attagatttt    1380
tcaagggctc ccattgaagt cctggctgaa accatgccaa tcctggaaca acgtaacttg    1440
aaggataagt tggaagtttt cgtggacggt ggtgttcgtc gtggtacaga tgtcttgaaa    1500
gcgttatgtc taggtgctaa aggtgttggt ttgggtagac cattcttgta tgcgaactca    1560
tgctatggtc gtaatggtgt tgaaaaagcc attgaaattt taagagatga aattgaaatg    1620
tctatgagac tattaggtgt tactagcatt gcggaattga agcctgatct tttagatcta    1680
tcaacactaa aggcaagaac agttggagta ccaaacgacg tgctgtataa tgaagtttat    1740
gagggaccta ctttaacaga atttgaggat gcatga                              1776
```

<210> SEQ ID NO 25
<211> LENGTH: 391
<212> TYPE: PRT
<213> ORGANISM: Saccharomyces cerevisiae

<400> SEQUENCE: 25

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile

```
                225                 230                 235                 240
Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
                260                 265                 270

Leu Gly Glu Ile Ile Arg Phe Gly Gln Met Phe Pro Glu Ser Arg
            275                 280                 285

Glu Glu Thr Tyr Tyr Gln Glu Ser Ala Gly Val Ala Asp Leu Ile Thr
        290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
                340                 345                 350

Thr Cys Gly Ser Val Glu Asp Phe Pro Leu Phe Glu Ala Val Tyr Gln
                355                 360                 365

Ile Val Tyr Asn Asn Tyr Pro Met Lys Asn Leu Pro Asp Met Ile Glu
            370                 375                 380

Glu Leu Asp Leu His Glu Asp
385                 390

<210> SEQ ID NO 26
<211> LENGTH: 1176
<212> TYPE: DNA
<213> ORGANISM: Saccharomyces cerevisiae

<400> SEQUENCE: 26
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actggggtac tactattgcc aaggtggttg ccgaaaattg taagggatac     180
ccagaagttt cgctccaat agtacaaatg tgggtgttcg aagaagagat caatggtgaa     240
aaattgactg aaatcataaa tactagacat caaaacgtga atacttgcc tggcatcact     300 ctacccgaca atttggttgc taatccagac ttgattgatt cagtcaagga tgtcgacatc     360
atcgttttca acattccaca tcaattttg ccccgtatct gtagccaatt gaaaggtcat     420
gttgattcac acgtcagagc tatctcctgt ctaaagggtt ttgaagttgg tgctaaaggt     480
gtccaattgc tatcctctta catcactgag gaactaggta ttcaatgtgg tgctctatct     540
ggtgctaaca ttgccaccga agtcgctcaa gaacactggt ctgaaacaac agttgcttac     600
cacattccaa aggatttcag aggcgagggc aaggacgtcg accataaggt tctaaaggcc     660
ttgttccaca gaccttactt ccacgttagt gtcatcgaag atgttgctgg tatctccatc     720
tgtggtgctt tgaagaacgt tgttgcctta ggttgtggtt tcgtcgaagg tctaggctgg     780
ggtaacaacg cttctgctgc catccaagaa gtcggtttgg gtgagatcat cagattcggt     840
caaatgtttt tcccagaatc tagagaagaa acatactacc aagagtctgc tggtgttgct     900
gatttgatca ccacctgcgc tggtggtaga aacgtcaagg ttgctaggct aatggctact     960
tctggtaagg acgcctggga atgtgaaaag gagttgttga atggccaatc cgctcaaggt    1020
ttaattacct gcaaagaagt tcacgaatgg ttggaaacat gtggctctgt cgaagacttc    1080
ccattatttg aagccgtata ccaaatcgtt tacaacaact acccaatgaa gaacctgccg    1140
gacatgattg aagaattaga tctacatgaa gattag                              1176
```

<210> SEQ ID NO 27
<211> LENGTH: 332
<212> TYPE: PRT
<213> ORGANISM: Pelodiscus sinensis

<400> SEQUENCE: 27

```
Met Ser Val Lys Glu Leu Leu Ile Gln Asn Val His Lys Glu Glu His
1               5                   10                  15

Ser His Ala His Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Arg Gly Glu Met Leu Asp
    50                  55                  60

Leu Gln His Gly Ser Leu Phe Leu Arg Thr Pro Lys Ile Val Ser Gly
65                  70                  75                  80

Lys Asp Tyr Ser Val Thr Ala His Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asp Cys Met Leu Leu Val Val Ser Asn Pro Val Asp Ile Leu Thr
    130                 135                 140

Tyr Val Ala Trp Lys Ile Ser Gly Phe Pro Lys His Arg Val Ile Gly
145                 150                 155                 160

Ser Gly Cys Asn Leu Asp Ser Ala Arg Phe Arg Tyr Leu Met Gly Glu
                165                 170                 175

Lys Leu Gly Ile His Ser Leu Ser Cys His Gly Trp Ile Ile Gly Glu
            180                 185                 190

His Gly Asp Ser Ser Val Pro Val Trp Ser Gly Val Asn Val Ala Gly
        195                 200                 205

Val Ser Leu Lys Ala Leu Tyr Pro Asp Leu Gly Thr Asp Ala Asp Lys
    210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Thr Val Met Lys Asn Leu Arg Arg Val His Pro
            260                 265                 270

Ile Ser Thr Met Val Lys Gly Met Tyr Gly Val Ser Ser Asp Val Phe
        275                 280                 285

Leu Ser Val Pro Cys Val Leu Gly Tyr Ala Gly Ile Thr Asp Val Val
    290                 295                 300

Lys Met Thr Leu Lys Ser Glu Glu Glu Lys Leu Arg Lys Ser Ala
305                 310                 315                 320

Asp Thr Leu Trp Gly Ile Gln Lys Glu Leu Gln Phe
                325                 330
```

<210> SEQ ID NO 28
<211> LENGTH: 999
<212> TYPE: DNA
<213> ORGANISM: Pelodiscus sinensis

<400> SEQUENCE: 28

```
atgtccgtaa aggaactact tatacaaaac gtccataagg aggagcattc tcacgctcac      60
aataagataa cagttgtagg agtaggtgca gtaggtatgg catgtgctat ttcgatatta     120
atgaaagact tggctgatga actagccttg gttgatgtga ttgaggataa gttacgtgga     180
gaaatgttag atttgcaaca tggttcattg ttcttgagaa cccccaaaat tgtctcgggt     240
aaggattatt cagtcactgc tcattctaaa ctggttatca ttacagcagg tgcaagacag     300
caagaagggg agagcagact aaatctggtt caacgtaatg tcaacatctt caagtttatc     360
atcccgaacg tagtaaaata cagtccagac tgcatgttgc ttgttgtgag taatccagtt     420
gacatcttaa cctatgttgc gtggaaaatc agtgggtttc caaaacatag ggtgattggc     480
tcaggatgca accttgatag cgccaggttt aggtatctaa tgggagaaaa attaggtatt     540
cactccttat cttgtcatgg ctggataata ggcgaacatg gtgattcttc ggtacctgtt     600
tggtccgggg ttaatgtggc tggtgttagt ttaaaagcat tatatcctga cctgggtact     660
gatgccgata aagaacattg gaaagaagtg cacaaacaag tggttgattc tgcttacgaa     720
gttattaaac ttaagggcta cacttcttgg gctataggtc tatcagtagc tgatttggca     780
gaaaccgtta tgaaaaattt aagaagagtc cacccaattt ccacgatggt caagggtatg     840
tacggtgtta gctctgacgt cttcttatct gttccttgtg ttttgggata tgcgggaatt     900
acagacgtcg tgaagatgac attgaaatca gaggaagagg aaaaactaag aaagtcagcc     960
gatactctgt ggggcattca aaaggaattg cagtttta                            999
```

POLYNUCLEOTIDE CONFERRING ACID TOLERANT PROPERTY TO YEAST CELL AND METHOD OF PRODUCING A PRODUCT BY USING THE YEAST CELL

CROSS-REFERENCE TO RELATED APPLICATIONS

This application claims the benefit of Korean Patent Application No. 10-2013-0104056, filed on Aug. 30, 2013, in the Korean Intellectual Property Office, the disclosure of which is hereby incorporated by reference.

INCORPORATION BY REFERENCE OF ELECTRONICALLY SUBMITTED MATERIAL

Incorporated by reference in its entirety herein is a computer-readable nucleotide/amino acid sequence listing submitted herewith and identified as follows: 56,900 bytes ASCII (Text) file named "716660_ST25.TXT," created Aug. 29, 2014.

STATEMENT REGARDING DEPOSIT OF BIOLOGICAL MATERIAL

This statement concerns the deposit of the following biological material:
Strain: *Saccharomyces cerevisiae* ΔPDC1::LDH, Δcyb2::LDH, ΔGPD::LDH SP1005 as Accession Number: KCTC 12415BP was deposited on May 30, 2013 and accepted by the following depository under the terms of the Budapest Treaty:
Korean Collection for Type Cultures
Korea Research Institute of Bioscience and Biotechnology (KRIBB)
125 Gwahak-ro, Yuseong-gu,
Daejeon 305-806,
Republic of Korea

BACKGROUND

1. Field

The present disclosure relates to a polypeptide conferring acid-tolerant property on a yeast cell, a polynucleotide encoding the polypeptide, a yeast cell including an increased amount of the polypeptide, a method of producing a product by using the yeast cell, and a method of producing an acid-tolerant yeast cell.

2. Description of the Related Art

Organic acids are widely used in a variety of industries. For example, lactate is an organic acid that is used in a variety of industrial fields, including food, pharmaceutical, chemical, and electronic industries. Lactate is a colorless, odorless, water-soluble, low-volatile material. Lactate is also not toxic to the human body, and is used as a flavoring agent, a sour taste agent, a preserving agent, or the like. Lactate is also used as a source of polylactic acid (PLA) that is an environmentally friendly, biodegradable plastic known as an alternate polymeric material.

Organic acids may be dissociated into hydrogen ions and their own negative ions at a higher pH than their own dissociation constant (pKa value), for example, under a neutral condition (e.g., a pH of about 7). Organic acids, for example, lactic acid, may be present in the form of free acid without an electromagnetic force at a pH lower than its own pKa value. The negative ion of an organic acid may not be permeable with respect to a cell membrane, but the organic acid may be permeable with respect to the cell membrane when it is present in the form of a free acid. Therefore, an organic acid in free acid form may flow into the cells from extracellular environments where the concentration of the organic acid is high, thus lowering intercellular pH level. Meanwhile, an organic acid present as negative ions requires an additional isolation process involving the addition of a salt. Cells lacking acid-tolerance may become inactive and nonviable under acidic conditions, such as in the case of lactic acid buildup within a cell.

Therefore, there is a need for microorganisms with acid-tolerance.

SUMMARY

Provided is a polypeptide having an amino acid sequence with a sequence identity of about 95% or greater with respect to SEQ ID NO: 1, wherein the polypeptide confers an acid tolerant property on a yeast cell.

Also provided is a polynucleotide encoding the polypeptide having an amino acid sequence with a sequence identity of about 95% or greater with respect to SEQ ID NO: 1.

Provided is a genetically modified acid-tolerant yeast cell having an increased amount of a polypeptide having an amino acid sequence with a sequence identity of about 95% or greater with respect to SEQ ID NO: 1.

Provided is an efficient method of producing a product by using the acid-tolerant yeast cell.

Provided is an efficient method of producing the acid-tolerant yeast cell.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
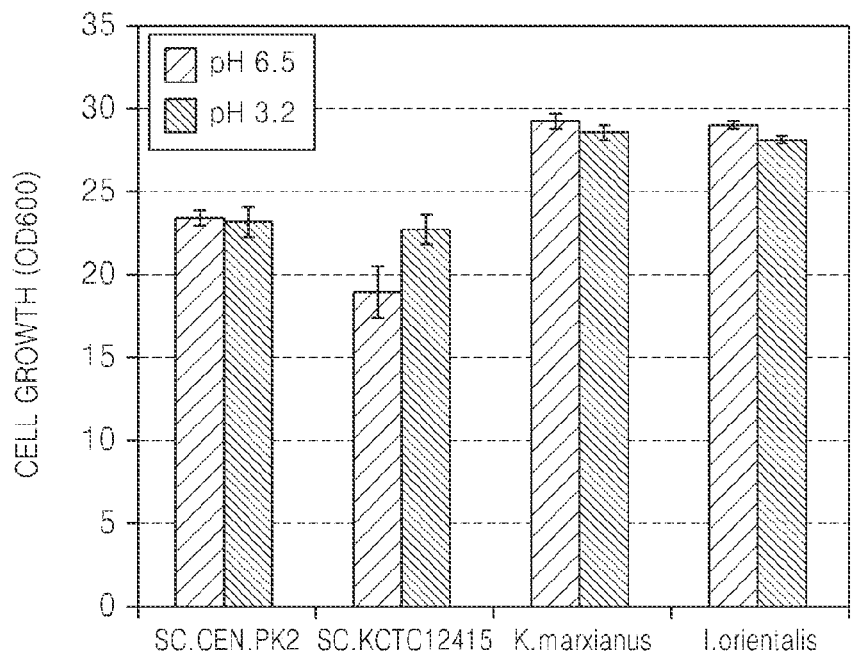
FIG. 1 is a graph displaying the $OD_{600}$ value of the yeast cells cultured at about 30° C. for about 22 hours in a YPD medium of which pH was adjusted using hydrochloric acid or potassium hydroxide to a pH of 3.2 or 6.5.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an embodiment of the present disclosure, there is provided a polypeptide conferring an acid-tolerant property on a yeast and having an amino acid sequence with a sequence identity of about 65%, (e.g., 95%) or greater with respect to SEQ ID NO: 1.

The yeast may belong to the phylum Ascomycota. The phylum Ascomycota may include the subphylum Saccharomycotina or subphylum Taphrinomycotina. The yeast may include the class Saccharomycetes or class Schizosaccharomycetes. The yeast may belong to the family Saccharomycetaceae. The family Saccharomycetaceae may include the genus *Brettanomyces, Candida, Citeromyces, Cyniclomyces, Debaryomyces, Issatchenkia, Kazachstania, Kluyveromyces, Komagataella, Kuraishia, Lachancea, Lodderomyces, Nakaseomyces, Pachysolen, Pichia, Saccharomyces, Spathaspora, Tetrapisispora, Vanderwaltozyma, Torulaspora, Williopsis, Zygosaccharomyces,* or *Zygotorulaspora*. For example, the yeast may be the genus *Candida, Issatchenkia, Kluyveromyces, Pichia, Saccharomyces, Torulaspora, Zygosaccharomyces, Zygotorulaspora,* or *Schizosaccharomyces*.

The genus *Saccharomyces* (S.) may be, for example, *S. cerevisiae, S. bayanus, S. boulardii, S. bulderi, S. cariocanus, S. cariocus, S. chevalieri, S. dairenensis, S. ellipsoideus, S. eubayanus, S. exiguus, S. florentinus, S. kluyveri, S. martiniae, S. monacensis, S. norbensis, S. paradoxus, S. pastorianus, S. spencerorum, S. turicensis, S. unisporus, S. uvarum,* or *S. zonatus*.

In some embodiments, the yeast cell may be a natural yeast cell or a variant yeast cell capable of producing a product of interest, such as an organic acid, for example, lactate (or lactic acid). For example, the variant yeast cell may have a tolerance to, for example, uracil, sulfaguanidine, sulfathiazole, azaserine, trimethoprim, or monofluoroacetate. The organic acid may be a C1-C20 organic acid (e.g., a hydrocarbon comprising a single carbon to about 20 carbons). The organic acid may be acetic acid, lactic acid, propionic acid, 3-hydroxypropionic acid, butyric acid, 4-hydroxy-butyric acid, succinic acid, fumaric acid, malic acid, oxalic acid, adipic acid, or a combination thereof.

In some embodiments, the polypeptide may have an amino acid sequence with a sequence identity of about 65% or greater with respect to SEQ ID NO: 1, for example, a sequence identity of about 70% or greater, about 80% or greater, about 90% or greater, about 91% or greater, about 92% or greater, about 93% or greater, about 94% or greater, about 95% or greater, about 96% or greater, about 97% or greater, about 98% or greater, about 99% or greater, or about 100%.

As used herein, the term "sequence identity" of a nucleic acid or polypeptide with respect to another nucleic acid or polypeptide refers to the degree of homology in nucleic acid or amino acid residues between a first polynucleotide or first polypeptide and a second polynucleotide or second polypeptide. The sequence identity is a value obtained via optimal alignment and comparison of the two sequences in the specific regions for comparison, in which a partial sequence in one of the compared specific regions may be added or deleted with respect to a reference sequence. The sequence identity as a percentage may be calculated by, for example, comparing two sequences which are in specific regions and are aligned to best match each other, determining match sites with the same amino acid or base in the two sequences to obtain the number of the match sites, dividing the number of the match sites in the two sequences by a total number of sites in the compared specific regions (i.e., a size of the compared region), and multiplying a result of the division by 100 to obtain a sequence identity as a percentage. The sequence identity as a percentage may be determined using a known sequence comparison program, for example, BLASTN(NCBI), CLC MAIN WORKBENCH(CLC BIO), MegAlign™ (DNASTAR INC.), or any other suitable sequence comparison program.

In identifying a polypeptide or polynucleotide with the same or similar function or activity with respect to various types of species, any various levels of sequence identity may be applied. In some embodiments, the polypeptide or polynucleotide may have an amino acid sequence/nucleic acid sequence with a sequence identity of, for example, 50% or greater, 55% or greater, 60% or greater, 65% or greater, 70% or greater, 75% or greater, 80% or greater, 85% or greater, 90% or greater, 95% or greater, 96% or greater, 97% or greater, 98% or greater, 99% or greater, or 100%, with respect to a second polypeptide or second polynucleotide the polypeptide or polynucleotide is compared to.

The polypeptide having an amino acid sequence with a sequence identity of about 65% or greater, for example about 95% or greater with respect to SEQ ID NO: 1 may be derived from bacteria, yeasts, or fungi, for example, selected from the group consisting of the genus *Aspergillus, Candida, Coccidioides, Cryptococcus, Debaryomyces, Eromothecium, Fusarium, Issatchenkia, Kluyveromyces, Magnaporthe, Neurospora, Neosartorya, Paracoccidioides, Pneumocystis, Saccharomyces, Schizosaccharomyces, Yarrowia, Torulaspora,* and *Zygosaccharomyces*. For example, the polypeptide may be derived from *Aspergillus nidulans, Aspergillus oryzae, Agipergillus kawachii, Aspergillus flavus, Candida albicans, Candida dubliniensis, Candida glabrata, Candida maltose, Coccidioides posadasii, Cryptococcus neoformans, Debaryomyces hansenii, Eromothecium gossypii, Fusarium oxysporum, Issatchenkia orientalis, Kluyveromyces lactis, Kluyveromyces thermotolerans, Magnaporthe grisea, Neurospora crassa, Neosartorya fumigate, Paracoccidioides brasiliensis, Pneumocystis carinii, Saccharomyces cerevisiae, Schizosaccharomyces pombe, Schizosaccharomyces japonicus, Yarrowia lipolytica, Zygosaccharomyces bailii,* or the like.

The polypeptide may have an activity similar to or the same as beta-1,3-glucanosyltransferase (GAS). The polypeptide may belong to an enzyme with an enzyme code of EC 2.4.1.-.

According to another embodiment of the present disclosure, provided is a polynucleotide encoding any of the polypeptides according to the above-described embodiments conferring an acid-tolerant property on a yeast and having an amino acid sequence with a sequence identity of about 65% or greater with respect to SEQ ID NO: 1.

In some embodiments, the polynucleotide may have a nucleotide sequence of at least one of SEQ ID Nos. 2, 3, 4, and 5. SEQ ID NO: 2 indicates a coding sequence encoding the polypeptide of SEQ ID NO: 1. SEQ ID Nos. 3, 4, and 5 indicate three variant sequences of the coding sequence of SEQ ID NO: 2 that include part of 5'-UTR and 3'-UTR sequences of *Issatchenkia orientalis* ATCC 20381. The polynucleotide may be non-wild-type and obtained via artificial process. The polynucleotide may be a polynucleotide or cDNA without an intron. The polynucleotide may be isolated.

According to another embodiment of the present disclosure, there is provided a composition including a polynucleotide encoding any of the polypeptides according to the above-described embodiments conferring an acid-tolerant property on a yeast and having an amino acid sequence with a sequence identity of about 65% or greater, for example, about 95% or greater with respect to SEQ ID NO: 1. Accordingly, the composition may confer the acid-tolerant property on the yeast.

According to another embodiment of the present disclosure, there is provided a yeast cell having acid tolerance (e.g., a modified or recombinant yeast cell having increased acid tolerance as compared to a unmodified (wild-type) yeast cell of the same species). The yeast cell may include an increased amount of a polypeptide having an amino acid sequence with a sequence identity of about 95% or greater with respect to SEQ ID NO: 1, an increased amount of beta-1,3-glucanosyltransferase (GAS), or both, as compared to a wild-type or unmodified yeast of the same species.

The beta-1,3-glucanosyltransferase (GAS) may be derived from a yeast, for example, with an enzyme code of EC 2.4.1.-. The yeast may belong to the phylum Ascomycota. The phylum Ascomycota may include the subphylum Saccharomycotina or subphylum Taphrinomycotina. The yeast may include the class Saccharomycetes or class Schizosaccharomycetes. The yeast may belong to the family Saccharomycetaceae. The family Saccharomycetaceae may include the genus *Brettanomyces, Candida, Citeromyces, Cyniclomyces, Debaryomyces, Issatchenkia, Kazachstania, Kluyveromyces, Komagataella, Kuraishia, Lachancea, Lodderomyces, Nakaseomyces, Pachysolen, Pichia, Saccharomyces, Spathaspora, Tetrapisispora, Vanderwaltozyma, Torulaspora, Williopsis, Zygosaccharomyces,* or *Zygotorulaspora*. For example, the yeast may be the genus *Candida, Issatchenkia, Kluyveromyces, Pichia, Saccharomyces, Torulaspora, Zygosaccharomyces, Zygotorulaspora,* or *Schizosaccharomyces*.

The genus *Saccharomyces* (S.) may include, for example, *S. cerevisiae, S. bayanus, S. boulardii, S. bulderi, S. cariocanus, S. cariocus, S. chevalieri, S. dairenensis, S. ellipsoideus, S. eubayanus, S. exiguus, S. florentinus, S. kluyveri, S. martiniae, S. monacensis, S. norbensis, S. paradoxus, S. pastorianus, S. spencerorum, S. turicensis, S. unisporus, S. uvarum,* or *S. zonatus*. The beta-1,3-glucanosyltransferase may be derived from *S. cerevisiae*. The beta-1,3-glucanosyltransferase may be, for example, at least one of GAS1, 2, 3, 4, and 5 derived from *S. cerevisiae*, and a polypeptide having an amino acid sequence with a sequence identity of about 65% or greater, for example, about 95% or greater with respect to SEQ ID NO: 1.

The increased amount of the polypeptide and/or the beta-1,3-glucanosyltransferase in the yeast cell may be attributed to increased expression of a gene encoding the polypeptide having an amino acid sequence with a sequence identity of about 65% or greater, for example, about 95% and/or greater with respect to SEQ ID NO: 1. The increase in the amount of the polypeptide and/or the beta-1,3-glucanosyltransferase may be about 0.1% or greater, about 1% or greater, about 5% or greater, about 10% or greater, about 15% or greater, about 20% or greater, about 30% or greater, about 50% or greater, about 60% or greater, about 70% or greater, or about 100% or greater with respect to a control group. The control group, for example, may be a yeast cell not manipulated to increase the amount of the polypeptide or beta-1,3-glucanosyltransferase (e.g., a "wild-type" yeast). The control group may be a yeast cell not containing the polypeptide.

The increased expression may be attributed to the introduction of a gene encoding the polypeptide having an amino acid sequence with a sequence identity of about 65% or greater, for example about 95% or greater with respect to SEQ ID NO: 1. The yeast cell into which the gene is introduced may be a type that inherently (naturally) includes the gene or may be a type that does not normally include the gene (i.e., the gene is heterologous to the yeast cell). The gene may be operably linked to a regulatory site that enables expression of the gene, for example, a promoter, an enhancer, a polyadenylation site, or a combination thereof. The gene may be inserted into a genome of the yeast cell or may be in a non-genomic site of the yeast cell. The introduction of the gene may increase the number of expressible functional copies of the gene, for example, to a number of 1 or greater, a number of 10 or greater, a number of 100 or greater, or a number of 1,000 or greater. For example, the increased number of the expressible functional copies of the gene may be from about 1 to about 1,000, from about 1 to about 100, from about 1 to about 50, from about 1 to about 10, from about 1 to about 5, or from about 1 to about 3.

The introduction of the gene may be implemented via a known method, for example, transformation, transfection, or electroporation. The introduction of the gene may also be conducted by any known transformation method for yeast may be used. Such a transformation method may, for example, be a conventional method like lithium acetate method, electroporation method, spheroplast method, glass-beads method, or the like. Further, a commercially available yeast transformation kit may be used. The gene may be introduced itself, or via vehicle such as vector, for example, viral vector or plasmid vector. The gene may be introduced by using a vehicle or directly on its own. As used herein, the term "vehicle" refers to a nucleic acid molecule able to deliver other nucleic acids linked thereto. As a nucleic acid sequence mediating introduction of a specific gene, the vehicle used herein is construed to be interchangeable with a vector, a nucleic acid construct, and/or a cassette. Examples of the vector are a plasmid vector and a virus-derived vector. A plasmid is a circular double-stranded DNA molecule linkable with another DNA. Non-limiting examples of the vector used in the present disclosure are a plasmid expression vector, and a virus expression vector, such as a replication-defective retrovirus, adenovirus, adeno-associated virus (AAV), or a combination thereof. A yeast expression vector may be a vector for gene expression in, for example, *S. cerevisiae*. Suitable examples of the yeast expression vector are pYepSec1, 2i, pAG-1, Yep6, Yep13, PEMBLYe23, pMFa, pJRY88, or pYES2. The expression vector may be heterologous to the yeast cell.

The increased expression may be attributed to amplification or modification of an inherent gene or modification of a regulatory site of the inherent gene. The amplification of the inherent gene may include incubating the yeast cell under a selection pressure, for example, auxotrophic condition, or antibiotic selection pressure, so that desired modified yeast cell can be selected. The modification of a regulatory site of the inherent gene may include changing the sequence of promoter, transcription terminator, operator, and the like by a site specific mutation method, or homologous recombination method. Modification of the inherent gene may include change the coding sequence of a gene by a site specific mutation method, or homologous recombination method. The modification may be insertion, substitution, conversion, or addition.

The yeast with acid tolerance may belong to the phylum Ascomycota. The phylum Ascomycota may include the subphylum Saccharomycotina or subphylum Taphrinomycotina. The acid-tolerant yeast may include the class Saccharomycetes or class Schizosaccharomycetes. The acid-tolerant yeast may belong to the family Saccharomycetaceae. The family Saccharomycetaceae may include the genus *Brettanomyces, Candida, Citeromyces, Cyniclomyces, Debaryomyces, Issatchenkia, Kazachstania, Kluyveromyces, Komagataella, Kuraishia, Lachancea, Lodderomyces, Nakaseomyces, Pachysolen, Pichia, Saccharomyces, Spathaspora, Tetrapisispora, Vanderwaltozyma, Torulaspora, Williopsis, Zygosaccharomyces*, or *Zygotorulaspora*. For example, the acid-tolerant yeast may be the genus *Candida, Issatchenkia, Kluyveromyces, Pichia, Saccharomyces, Torulaspora, Zygosaccharomyces, Zygotorulaspora*, or *Schizosaccharomyces*.

The genus *Saccharomyces* (S.) may include, for example, *S. cerevisiae, S. bayanus, S. boulardii, S. bulderi, S. cariocanus, S. cariocus, S. chevalieri, S. dairenensis, S. ellipsoideus, S. eubayanus, S. exiguus, S. florentinus, S. kluyveri, S. martiniae, S. monacensis, S. norbensis, S. paradoxus, S. pastorianus, S. spencerorum, S. turicensis, S. unisporus, S. uvarum*, or *S. zonatus*.

The term "acid tolerance," "acid-tolerant, or acid tolerating" used herein refer to the ability of a yeast cell to survive or grow under acidic conditions better than a non-manipulated yeast cell, for example, genetically non-manipulated cell. The acidic conditions may include an organic acid, an inorganic acid, or a combination thereof. The organic acid may be a C1-C20 organic acid. The organic acid may be acetic acid, lactic acid, propionic acid, 3-hydroxy propionic acid, butyric acid, 4-hydroxy butyric acid, succinic acid, fumaric acid, malic acid, oxalic acid, adipic acid, hydrochloric acid, a sulfuric acid, or a combination thereof. Accordingly, the yeast cell having the acid tolerance may grow better at a pH of about 2.0 to about 7.0, for example, at a pH of about 2.0 to about 5.0, at a pH of about 2.0 to about 4.0, at a pH of about 2.0 to about 3.8, at a pH of about 2.5 to about 3.8, at a pH of about 3.0 to about 3.8, at a pH of about 2.0 to about 3.0, at a pH about 2.0 to about 2.7, at a pH of about 2.0 to about 2.5, or at a pH of about 2.5 to about 3.0, than a yeast cell in which the amount of a polypeptide having an amino acid sequence with a sequence identity of about 65% or greater, for example, about 95% or greater with respect to SEQ ID NO: 1 is not increased compared to an unmodified (wild-type) yeast cell of the same species.

The term "acid tolerance" used herein may also refer to a higher metabolization ability of a yeast cell under acidic conditions than a non-manipulated cell, genetically non-manipulated cell. The higher metabolization ability may include faster or better metabolic ability, faster growth, and/or higher cell viability than a non-manipulated cell, genetically non-manipulated cell. The acidic conditions may include an organic acid, an inorganic acid, or a combination thereof. The organic acid may be a C1-C20 organic acid. The organic acid may be acetic acid, lactic acid, propionic acid, 3-hydroxy propionic acid, butyric acid, 4-hydroxy butyric acid, succinic acid, fumaric acid, malic acid, oxalic acid, adipic acid, hydrochloric acid, a sulfuric acid, or a combination thereof. Accordingly, the yeast cell having the acid tolerance may have higher metabolization ability at a pH of about 2.0 to about 7.0, for example, at a pH of about 2.0 to about 5.0, at a pH of about 2.0 to about 4.0, at a pH of about 2.0 to about 3.8, at a pH of about 2.5 to about 3.8, at a pH of about 3.0 to about 3.8, at a pH of about 2.0 to about 3.0, at a pH of about 2.0 to about 2.7, at a pH of about 2.0 to about 2.5, or at a pH of about 2.5 to about 3.0, than a yeast cell in which the amount of a polypeptide having an amino acid sequence with a sequence identity of about 65% or greater, for example about 95% or greater with respect to SEQ ID NO: 1 is not increased. The degree of metabolization ability may be measured as a nutrient absorption rate of a cell, for example, a glucose absorption rate of a cell. In some embodiment, the degree of metabolization ability may also be measured as a metabolite excretion rate of a cell, for example, a carbon dioxide excretion rate of a cell.

In some embodiments, the yeast cell may be a natural yeast cell, or a variant yeast cell for producing a product, for example, an organic acid, such as lactate. The variant yeast cell may include an enhanced activity of a protein involved in the synthesis of the product. For example, the variant yeast cell may be a cell obtained by introducing a gene encoding a protein involved in the synthesis of the product, by amplifying or modifying an inherent gene to increase expression of the gene, or by modifying a regulatory site of the inherent gene. The variant yeast cell may be a cell in which a gene encoding a protein involved in the degradation of the product is inactivated or attenuated.

As used herein, the term "inactivation" may refer to generation of a gene that is rendered unexpressible or a gene that is expressible but produces a product having no activity. The term "attenuation" may refer to generation of a less expressible gene compared to the expressibility of said gene in a non-manipulated yeast cell, for example, a genetically non-manipulated yeast cell, or a gene that is expressible but produces a product with lower activity than a non-manipulated yeast cell, for example, a genetically non-manipulated yeast cell. For example, the activity of a polypeptide encoded by such a gene may be lower than a non-manipulated control group by about 50% or greater, about 55% or greater, about 60% or greater, about 70% or greater, about 75% or greater, about 80% or greater, about 85% or greater, about 90% or greater, about 95% or greater, or about 100%.

The inactivation or attenuation may be performed by a selective method or a non-selective method. For example, the selective method may be a homologous recombination method. The homologous recombination method may involve transforming vectors including partial sequences of the gene into cells, culturing the cells to allow homologous recombination of the partial sequences with endogenous genes of the cells, and screening the cells where the homologous recombination occurred by using a selective marker. The selective marker may be a marker for auxotrophy, tolerance to a cell-poisoning agent, or a selectable phenotype, such as for expression of a surface protein.

In some embodiments, the product produced from the yeast cell as described above may be an organic acid, a protein, a fat, or a sugar. The product may be present as a free compound without charges, for example, negative charges, at a specific level of acidity or less. Accordingly, it may be unnecessary to convert the product into the form of a salt by using counter ions in order to isolate the product. The product may be an organic acid. For example, the organic acid may be a C1-C20 organic acid. The organic acid may be, for example, acetic acid, lactic acid, propionic acid, 3-hydroxy propionic acid, butyric acid, 4-hydroxy butyric acid, succinic acid, fumaric acid, malic acid, citric acid, oxalic acid, adipic acid, or a combination thereof.

In some embodiments, the yeast cell may be a cell with increased activity of a protein involved in the synthesis of lactic acid. The increased activity of the protein may be obtained from increased expression of a gene encoding the protein involved in the synthesis of lactic acid. For example, the increased activity of the protein may be obtained by introducing a gene encoding the protein involved in the synthesis of lactic acid, amplifying or modifying an inherent gene to increase expression of the gene encoding the protein, or modifying a regulatory site of the inherent gene. The increased activity of the protein may be higher than that of a control group by, for example, about 5% or greater, about 10% or greater, about 15% or greater, about 20% or greater, about 30% or greater, about 50% or greater, about 60% or greater, about 70% or greater, or about 100% or greater. The control group may be a non-manipulated yeast cell, for example, a genetically non-manipulated yeast cell or a parent yeast cell.

The protein involved in the synthesis of lactic acid may be, for example, lactate dehydrogenase with the activity of converting pyruvate into lactate. The activity of the lactate dehydrogenase may be increased to be sufficient to produce lactate.

The "lactate dehydrogenase (LDH)" may be an enzyme catalyzing conversion of pyruvate into lactate. The lactate dehydrogenase may be a NAD(P)-dependent enzyme, and may act on or produce either L-lactate or D-lactate. The NAD(P)-dependent enzyme may be an enzyme of EC 1.1.1.27 acting on or producing L-lactate, or a yeast of EC 1.1.1.28 acting on or producing D-lactate. The lactate dehydrogenase may have an amino acid sequence of SEQ ID NO: 19. A gene encoding the lactate dehydrogenase may have a nucleotide sequence of SEQ ID NO: 20. The lactate dehydrogenease having an amino acid sequence of SEQ ID NO: 19 and the gene encoding the lactate dehydrogenase of SEQ ID NO: 20 may be derived from Sordaria macrospora. The lactate dehydrogenase may have an amino acid sequence of SEQ ID NO: 27. A gene encoding the lactate dehydrogenase may have a nucleotide sequence of SEQ ID NO: 28. The lactate dehydrogeneases having an amino acid sequence of SEQ ID NO: 27 and the gene encoding the lactate dehydrogenase of SEQ ID NO: 28 may be derived from Pelodiscus sinensis japonicus.

In some embodiments, the yeast cell may include a removed or decreased activity of a protein involved in breakdown of lactic acid or a removed or decreased activity of a protein involved in an inhibition of a production of lactic acid. The removed or decreased activity of the protein may be from inactivation or attenuation of a gene encoding the protein involved in breakdown of lactic acid. The protein involved in breakdown of lactic acid may be a polypeptide with the activity of converting pyruvate into acetaldehyde, for example, pyruvate decarboxylase (PDC); a polypeptide with the activity of converting lactate into pyruvate, for example, lactate cytochrome-c oxidoreductase (CYB2); a polypeptide with the activity of converting dihydroxyacetone phosphate (DHAP) into glycerol-3-phosphate, for example, cytosolic glycerol-3-phosphate dehydrogenase (GPD1); or a combination thereof. The decreased activity of the protein may be lower than that of a control group by, for example, about 10% or greater, about 20% or greater, about 30% or greater, about 40% or greater, about 50% or greater, about 55% or greater, about 60% or greater, about 70% or greater, about 75% or greater, about 80% or greater, about 85% or greater, about 90% or greater, about 95% or greater, or about 100%. The control group may be a non-manipulated yeast cell, for example, a genetically non-manipulated yeast cell or a parent yeast cell.

The inactivation or attenuation of a gene encoding the protein involved in breakdown of lactic acid may be attained by transforming vectors including partial sequences of the gene encoding the protein involved in breakdown of lactic acid into cells, culturing the cells to allow homologous recombination of the partial sequences with endogenous genes of the cells, and screening the cells where the homologous recombination occurred by using a selective marker. The selective marker may be a marker for using a selectable phenotype, such as product-tolerance such as a antibiotic tolerance, auxotrophy, tolerance to cell-poisoning agent, or expression of a surface protein.

The polypeptide with the activity of converting pyruvate into acetaldehyde may be an enzyme of EC 4.1.1.1. The polypeptide with the activity of converting pyruvate into acetaldehyde may have an amino acid sequence of SEQ ID NO: 21. A gene encoding the polypeptide with the activity of converting pyruvate into acetaldehyde may have a nucleotide sequence of SEQ ID NO: 22, and may be, for example, pdc1 or pdc2 encoding pyruvate decarboxylase (PDC). The polynucleotide encoding PDC of SEQ ID NO: 21 such as the polypeptide of SEQ ID NO: 22 may be derived from Saccharomyces cerevisiae.

The polypeptide with the activity of converting lactate into pyruvate may be a cytochrome c-dependent enzyme. The polypeptide with the activity of converting lactate into pyruvate may be lactate cytochrome-c oxidoreductase (CYB2). The lactate cytochrome c-oxidoreductase may be an enzyme of EC 1.1.2.4 acting on D-lactate, or a yeast of EC 1.1.2.3 acting on L-lactate. The polypeptide with the activity of converting lactate into pyruvate may have an amino acid sequence of SEQ ID NO: 23. A gene encoding the polypeptide with the activity of converting lactate into pyruvate may have a nucleotide sequence of SEQ ID NO: 24. The gene encoding CYB2 of SEQ ID NO: 23 such as gene of SEQ ID NO: 24 may be derived from Saccharomyces cerevisiae.

The polypeptide with the activity of converting dihydroxyacetone phosphate (DHAP) into glycerol-3-phosphate may be an enzyme catalyzing reduction of DHAP into glycerol-3-phosphate by using a reducing power obtained an oxidation of NADH into NAD+. In this regard, the enzyme may be an enzyme of EC 1.1.1.8. The polypeptide with the activity of converting dihydroxyacetone phosphate (DHAP) into glycerol-3-phosphate may be cytosolic glycerol-3-phosphate dehydrogenase (GDP1). The polypeptide with the activity of converting dihydroxyacetone phosphate (DHAP) into glycerol-3-phosphate may have an amino acid sequence of SEQ ID NO: 25. A gene encoding the polypeptide with the activity of converting dihydroxyacetone phosphate (DHAP) into glycerol-3-phosphate may have a nucleotide sequence of SEQ ID NO: 26, and may be, for example, gdp1 encoding glycerol-3-phosphate dehydrogenase.

In some embodiments, the yeast cell may be a yeast cell with Accession No. KCTC 12415 BP including a gene encoding an amino acid sequence with a sequence identity of about 65% or greater, for example about 65% or greater with respect to SEQ ID NO: 1.

According to another embodiment of the present disclosure, provided is a method of producing a product by using an acid-tolerant yeast cell described herein. The method includes: culturing the acid-tolerant yeast cell in a medium, the acid-tolerant yeast cell including an increased amount of a polypeptide having an amino acid sequence with a sequence identity of about 65% or greater, for example about 95% or greater with respect to SEQ ID NO: 1 or an increased amount of beta-1,3-glucanosyltransferase, or both; whereby the acid-tolerant yeast cell generates a product, and isolating the product from the culture. All other aspects of the acid-tolerant yeast cell are as previously described.

The culturing may be performed in a medium including a carbon source, for example, glucose. The medium for culturing the yeast cell may be any medium appropriate for growth of a host cell, for example, a minimal or complex medium including appropriate supplements. These appropriate media may be commercially purchasable or may be prepared by a known method.

The medium for culturing the yeast cell may be a medium satisfying the requirements for a specific yeast cell selected based on a target product. The medium may include at least one selected from the group consisting of a carbon source, a nitrogen source, a salt, a trace element, and a combination thereof.

A condition for the culturing may be controlled to be appropriate for producing a target product, for example, lactate. The culturing may be performed in an aerobic condition for cell proliferation. Optionally, the culturing in an aerobic condition may be followed by culturing in an anaerobic condition to produce the target product, for example, lactate. For example, the anaerobic condition for culturing may be a microaerobic condition with a dissolved oxygen (DO) concentration of about 0% to about 10%, and in some embodiments, about 0% to about 8%, about 0% to about 6%, about 0% to about 4%, about 0% to about 2%, about 0.1% to about 10%, about 1% to about 10%, about 2% to about 10%, about 3% to about 10%, about 4% to about 10%, about 5% to about 10%, about 6% to about 10%, about 7% to about 10%, about 8% to about 10%, about 9% to about 10%, about 1% to about 8%, about 2% to about 8%, about 3% to about 8%, about 4% to about 8%, about 5% to about 8%, about 6% to about 8%, about 7% to about 8%, about 1% to about 6%, about 2% to about 6%, about 3% to about 6%, about 4% to about 6%, about 5% to about 6%, about 1% to about 5%, about 2% to about 5%, about 2% to about 4%, or about 2% to about 5%.

As used herein, the term "culturing condition" refers to a condition for culturing the yeast cell. The culturing condition may be, for example, a condition including a carbon source or a nitrogen source utilized by the yeast cell, or an oxygen condition for the yeast cell. The carbon source for the yeast cell may include a monosaccharide, a disaccharide, or a polysaccharide. For example, the carbon source may include glucose, fructose, mannose, or galactose. The nitrogen source may be an organic nitrogen compound or an inorganic nitrogen compound. For example, the nitrogen source may be amino acid, amide, amine, nitrate, or ammonium salt. The oxygen condition for culturing the yeast cell may be an aerobic condition at a normal oxygen partial pressure, a low-oxygen condition for example including about 0.1% to about 10% of a saturation concentration for an oxygen in the air, or an anaerobic condition including no oxygen. A metabolic pathway of the yeast cell may be appropriately varied depending on practically available carbon and nitrogen sources.

The culturing may be performed under acidic conditions for an entire or partial period thereof. For example, the acidic condition may be at a pH of about 2.0 to about 7.0, and in some embodiments, at a pH of about 2.0 to about 5.0, at a pH of about 2.0 to about 4.0, at a pH of about 2.0 to about 3.8, at a pH of about 2.5 to about 3.8, at a pH of about 3.0 to about 3.8, at a pH of about 2.0 to about 3.0, at a pH of about 2.0 to about 2.7, at a pH of about 2.0 to about 2.5, or at a pH of about 2.5 to about 3.0.

The product produced from the yeast cell by the method may be an organic acid, a protein, a fat, or a sugar. For example, the product may be present as a free compound without charges, for example, negative charges, at a specific level of acidity or less. Accordingly, it may be unnecessary to convert the product into the form of a salt by using counter ions in order to isolate the product. The product may be an organic acid. For example, the organic acid may be a C1-C20 organic acid. The organic acid may be, for example, acetic acid, lactic acid, propionic acid, 3-hydroxy propionic acid, butyric acid, 4-hydroxy butyric acid, succinic acid, fumaric acid, malic acid, citric acid, oxalic acid, adipic acid, or a combination thereof.

The method of producing a product from an acid-tolerant yeast cell includes isolating the product from the culture. The isolating of the product may be performed using an appropriate method selected depending on the product. The isolating of the product may include isolating the product in the form of a free compound, such as a free acid, but not a salt form, from the culture.

In the method of producing a product from an acid-tolerant yeast cell, the yeast cell may be a yeast cell with Accession No. KCTC 12415 BP including a gene encoding an amino acid sequence with a sequence identity of about 65% or greater, for example about 95% or greater with respect to SEQ ID NO: 1, or a gene encoding beta-1,3-glucanosyltransferase. The product may be lactic acid.

According to another embodiment of the present disclosure, a method of producing an acid-tolerant yeast cell includes introducing a gene into the yeast cell, wherein the gene encodes a polypeptide having an amino acid sequence with a sequence identity of about 65% or greater, for example about 95% or greater with respect to SEQ ID NO: 1, or a gene encoding beta-1,3-glucanosyltransferase into the yeast cell.

The introduction of the gene may be conducted by any known transformation method for yeast may be used. Such a transformation method may, for example, be a conventional method like lithium acetate method, electroporation method, spheroplast method, glass-beads method, or the like. Further, a commercially available yeast transformation kit may be used. The gene may be introduced itself, or via vehicle such as vector, for example, viral vector or plasmid vector.

According to another embodiment of the present disclosure, a method of producing an acid-tolerant yeast cell includes genetically manipulating the yeast cell to increase expression of an inherent gene encoding a polypeptide having an amino acid sequence with a sequence identity of about 65% or greater, for example, about 95% or greater with respect to SEQ ID NO: 1 or an endogenous gene encoding beta-1,3-glucanosyltransferase.

The genetic manipulating may include amplifying the endogenous gene, manipulating a regulatory site of the endogenous gene, or manipulating a sequence of the endogenous gene. The genetic manipulating may include inserting, substituting, converting, or adding a nucleotide.

The amplifying of the endogenous gene may include incubating the yeast cell under a selection pressure, for example, auxotrophic condition, or antibiotic selection pressure, so that desired modified yeast cell can be selected. The manipulating a regulatory site of the endogenous gene may include changing the sequence of promoter, transcription terminator, operator, and the like by a site specific mutation method, or homologous recombination method. manipulating a sequence of the endogenous gene may include change the coding sequence of a gene by a site specific mutation method, or homologous recombination method.

The present invention will be described in further detail with reference to the following examples. These examples are for illustrative purposes only and are not intended to limit the scope of the invention.

EXAMPLE 1

Search for Acid-tolerant Strains and Genes (1) Search for Acid-Tolerant Strains

The inventors of the present disclosure cultured various strains under acidic conditions to identify yeast strains with a strong acid-tolerance.

In particular, *Saccharomyces cerevisiae* CEN.PK2-1 D (genotype: MATα ura3-52; trp1-289; leu2-3, 112; his3 Δ 1; MAL2-8$^C$; SUC2, EUROSCARF Accession No. 30000B), *Saccharomyces cerevisiae* Accession No. KCTC 12415 (CEN.PK2-1D (Δ pdc1::ldh Δ cyb2::ldhΔgpd1::ldh)), *Kluyveromyces maxianus* ATCC 36907, and *Issatchenkia orientalis* ATCC 20381 were cultured at an acidic pH in the presence of lactic acid to identify cell growth and glucose uptake rates (GUR). The KCTC 12415 strain used was a strain of which inherent genes of pyruvate decarboxylase (PDC1), L-lactate cytochrome-c-oxidoreductase (CYB2), and glycerol-3-phosphate dehydrogenase (GPD1), were inactivated via insertion by homogeneous recombination of a lactate dehydrogenase (LDH) gene derived from *Pelodiscus sinensis japonicus*.

Figure 2:
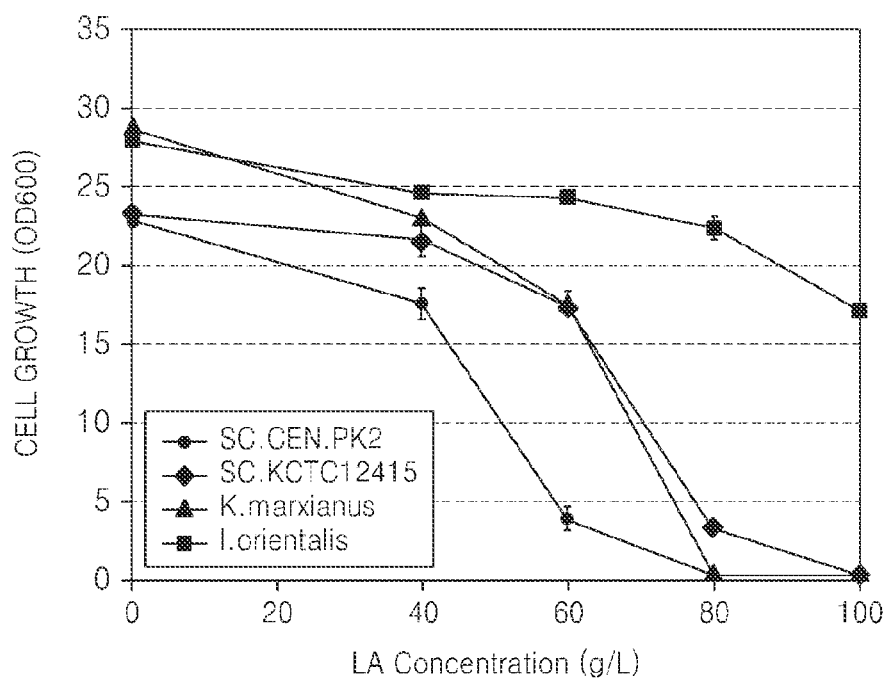
FIG. 2 is a cell growth curve displaying the $OD_{600}$ value of the yeast cells cultured at a pH of 3.2 at about 30° C. for about 22 hours in YPD media containing lactic acid.

FIGS. 1 and 2 are growth curves of the yeast cells cultured under acidic conditions in the presence of lactic acid.

FIG. 1 is a cell growth curve represented by $OD_{600}$ value of the yeast cells cultured at about 30° C. for about 22 hours in a YPD medium (including 10 g of yeast extract, 20 g of peptone, 20 g of glucose, and 20 g of lactic acid per 1 L of water) of which pH was adjusted using hydrochloric acid or potassium hydroxide to a pH of 3.2 or 6.5.

FIG. 2 is a cell growth curve represented by $OD_{600}$ value of the yeast cells cultured at a pH of 3.2 at about 30° C. for about 22 hours in YPD media containing varying amount of a lactic acid (LA).

Figure 3:
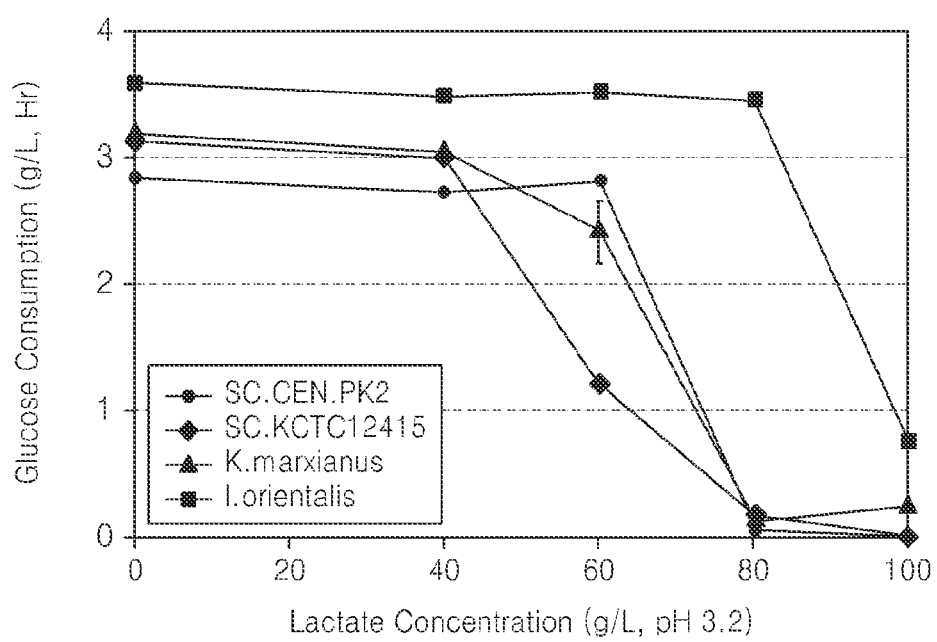
FIG. 3 is a graph displaying the glucose uptake rate (GUR) per hour of yeast cells cultured at a pH of 3.2 at about 30° C. for about 6 hours in YPD media containing varying amounts of a lactic acid (or lactate).

FIG. 3 is a graph of a glucose uptake rate (GUR) of the yeast cells cultured at a pH of 3.2 at about 30° C. for about 6 hours in YPD media containing varying amount of a lactic acid.

Referring to FIGS. 1 to 3, *Issatchenkia orientalis* ATCC 20381 was found to have a strong acid-tolerance, and nearly a normal cell activity up to a LA concentration of about 80 g/l or greater.

(2) Construction of cDNA Library of *Issatchenkia orientalis* ATCC 20381 and Search for Acid-Tolerant Gene (2.1) Vector for Library Construction A pRS426GPD vector (ATCC 87631) widely used for overexpression of genes in yeast cells was amplified via a polymerization chain reaction (PCR) using a primer pair of SEQ ID NOS: 6 and 8 and a primer pair of SEQ ID Nos. 7 and 9, followed by in-fusion cloning (Clontech, catalog #639690) to remove XbaI and PstI restriction enzyme sequences from a vector backbone to obtain a vector lacking the XbaI and PstI restriction enzyme sequence.

A vector with a full backbone lacking ampicillin resistance marker was amplified from the vector lacking the XbaI and PstI restriction enzyme sequences via a PCR using a primer pair of SEQ ID Nos. 10 and 11. A kanamycin resistance marker was amplified from pEGFP-C1 vector (Clontech, catalog #6084-1) via a PCR using a primer pair of SEQ ID Nos. 12 and 13, followed by subjecting the amplified DNA fragments in-fusion cloning (In-fusion kit, Clontech, catalog #639690) to substitute an ampicillin-tolerant bla gene as a selection marker of the vector with kanamycin-tolerant neo gene, thereby constructing a vector, which was named pRS426GPD-KanPX.

Figure 4:
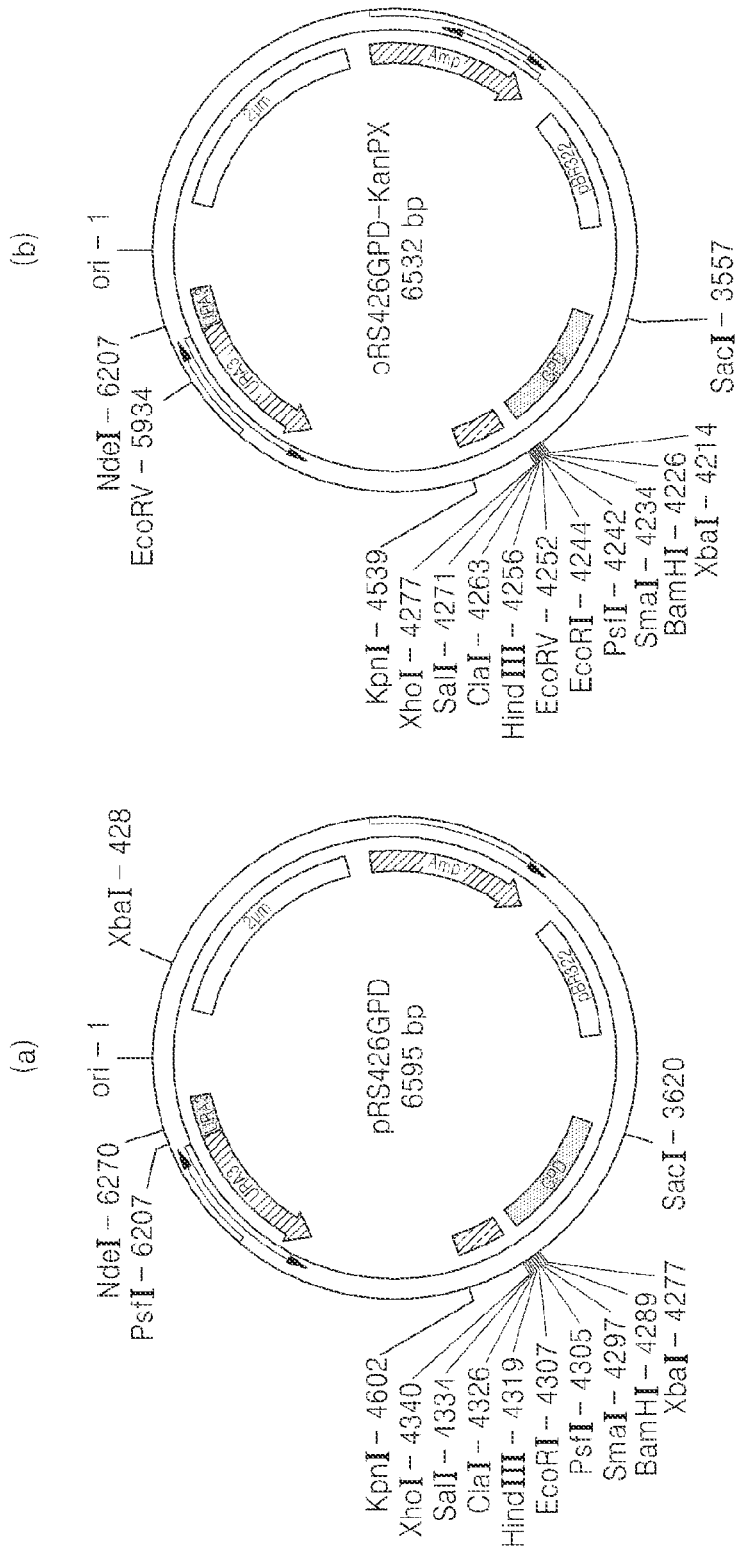
FIG. 4 illustrates maps of vectors pRS426GPD9 (a) and pRS426GPD-KanPX (b) used in constructing a cDNA library.

FIG. 4 illustrates maps of vectors pRS426GPD9 (a) and pRS426GPD-KanPX (b) used in constructing a cDNA library.

(2.2) cDNA Library Construction

Based on the result from the acid-tolerant strain screening (1) above, i.e., that the genotype of the *I. orientalis* strain expresses a phenotype of exhibiting strong acid tolerance, a cDNA library of genes of the *I. orientalis* strain is constructed, wherein the genes are genes overexpressed when cultured under acidic conditions. The acidic condition of a medium was created using lactic acid.

In particular, after the *I. orientalis* strain was cultured in a YPD medium (including 10 g of yeast extract, 20 g of peptone, and 20 g of glucose per 1 L of water) at about 30° C. for about 6 hours to an exponential phase where the growth rate was highest, the growth medium was changed to a YPD medium including 80 g/L of lactic acid and potassium hydroxide pH-adjusted to about a pH of 3.2 to reach a $OD_{600}$ of 1.0, followed by further culturing for about 2 hours.

After recovering all the cultured cells, RNA was separated and purified from the cells, and then used to synthesize cDNA. This cDNA was cloned into XbaI and XhoI restriction enzyme sites of a pRS426GPD-KanPX vector known as an overexpression vector of yeast genes, and then transformed in *Escherichia coli* (*E. coli*) to obtain a *E. coli* gene library. This gene library was subjected to a selection process using a kanamycin-included LB agar medium (including 10 g of trypton, 5 g of yeast extract, 10 g of sodium chloride (NaCl), 15 g of agar, and 25 mg of kanamycin per 1 L of water; and a pH of 7.0) to obtain a library size of about $2.5 \times 10^4$ clones. The resulting gene library was introduced into wild-type *Saccharomyces cerevisiae* CEN.PK2-1 D strain, thereby generating a yeast strain library having a size of about $4.0 \times 10^6$ clones.

(2.3) Acid-Tolerant Gene Selection from cDNA Library

The generated yeast strain library was smeared on a SD-URA agar plate, wherein the SD-URA includes 6.7 g of yeast nitrogen base, 1.92 g of a standard drop-out supplement without uracil, 20 g of glucose and 20 g of agar per 1 L of water; and 20 g/L of lactic acid and then incubated at about 30° C. for about 5 days, thereby screening about 800 yeast colonies. About 144 colonies exhibiting a good growth status from among the screened yeast colonies were subjected to a PCR using GPDpro-F primer of SEQ ID NO: 14 and CYC1-R3 primer of SEQ ID NO: 15, able to amplify inserts of the pRS426GPD-KanPX vector, to identify diversity of each variety of strain clones.

As a result, every clone was found to include an insert of a similar size of about 2 kb. About 16 colonies were selected from them to separate and purify a vector plasmid in yeast, which was then transformed into *E. coli* to recover a high concentration of plasmid DNA, followed by sequence analysis. As a result, common genes in every clone were found to be of three types of variants. These insert sequences including 5'-UTR and 3'-UTR were represented by SEQ ID Nos. 3, 4, and 5. The three inserts were variants with 5'-UTR sequence, but all of them encoded the same amino acid sequence of SEQ ID NO: 1, and a nucleotide sequence as a coding sequence was represented by SEQ ID NO: 2.

NCBI BLAST searches were conducted to search for a sequence with a sequence identity with an amino acid sequence of SEQ ID NO: 1. As a result, the searched protein was found to have homology with beta-1,3-glucanosyltransferase (GAS) proteins expressed in yeasts and a sequence identity of about 60% or less. This gene (encoding SEQ ID NO: 1) was named IoGAS1.

(3) Test of Function of Searched Acid-Tolerant Gene IoGAS1 pRS426GPD-KanPX vectors including IoGAS1 genes, i.e., the polynucleotides of SEQ ID NOS: 3 and 4, isolated from clone 1 and clone 2, respectively, were introduced into *Saccharomyces cerevisiae* Accession No. KCTC 12415 as a lactic acid producing strain, and then cultured to comparatively evaluate a lactic acid fermentation performance. The same lactic acid producing strain into which a pRS426GPD-KanPX vector was introduced was used as a control group.

To evaluate an effect of acid tolerance on a fermentation performance, each of the strains was inoculated onto an SD-URA medium (including 6.7 g of yeast nitrogen base, 1.92 g of a standard drop-out supplement without uracil, and 60 g of glucose, and pH-adjusted to 3.0 with HCl) at a pH of about 3.0, and then incubated in a microaerobic atmosphere containing about 2.5% of oxygen for about 40 hours while stirring at about 30° C. at 200 rpm. A sample was taken from the culture during the incubation to measure a cell concentration represented by an OD of about 600 nm, followed by centrifugation to remove the cell and collect a supernatant to measure the amounts of the residual glucose and produced lactic acid.

Figure 5:
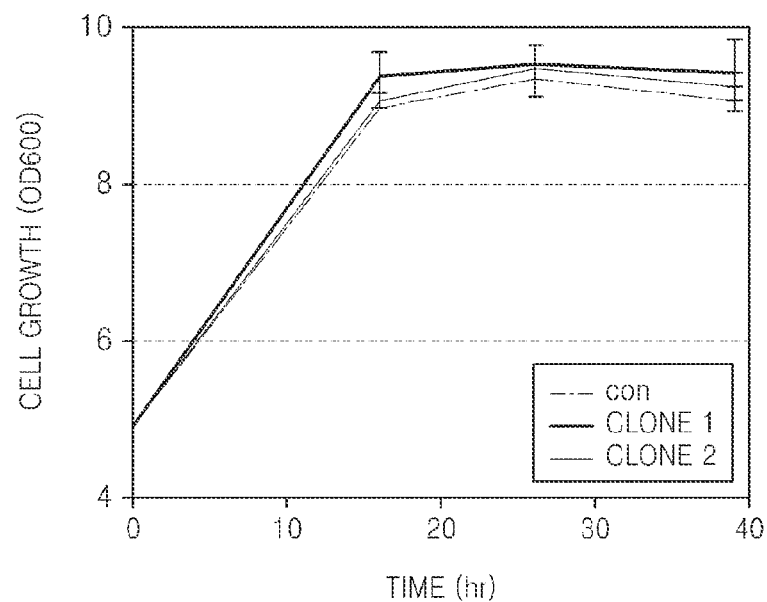
FIG. 5 is a graph of cell growth with respect to incubation time of yeast cells including IoGAS1.
Figure 6:
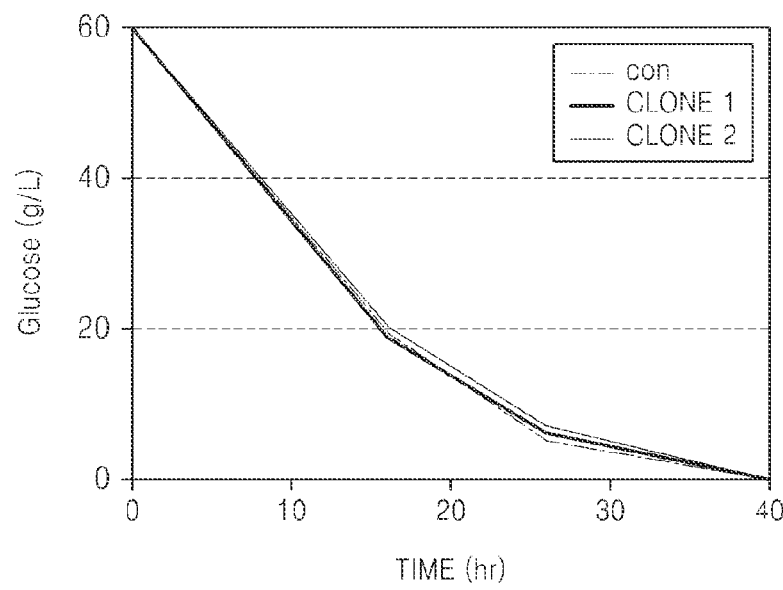
FIG. 6 is a graph of glucose concentration of yeast cell culture medium with respect to incubation time of yeast cells including IoGAS1.
Figure 7:
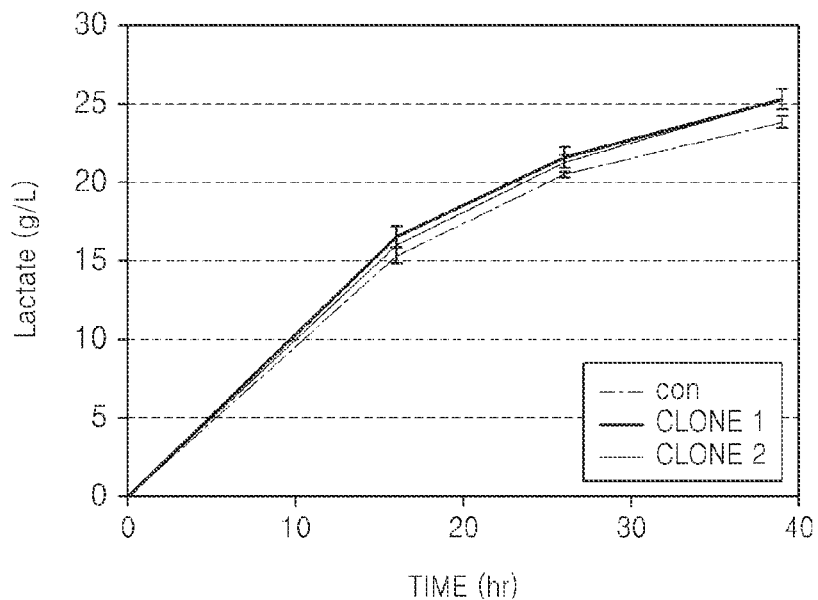
FIG. 7 is a graph of lactic acid concentration of cell culture medium with respect to incubation time of yeast cells including IoGAS1.
Figure 8:
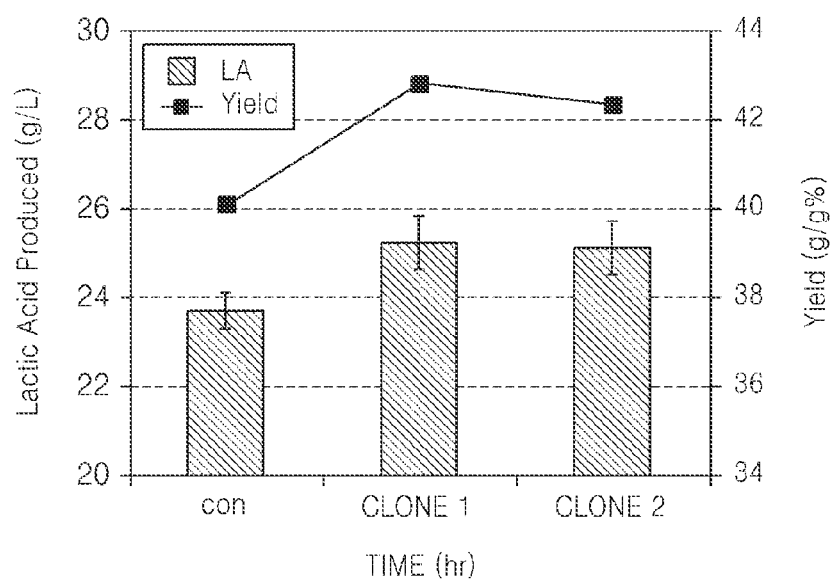
FIG. 8 illustrates the amount and yield of lactic acid produced by yeast cells including IoGAS1 from the incubation for about 40 hours.

FIGS. 5 to 8 are graphs illustrating the results of incubation of the lactic acid-producing yeast cells including the acid-tolerant gene IoGAS1. In particular, FIG. 5 is a graph of cell growth with respect to incubation time, FIG. 6 is a graph of glucose concentration with respect to incubation time, FIG. 7 is a graph of lactic acid concentration with respect to incubation time, and FIG. 8 illustrates graphs of amount and yield of lactic acid produced from the incubation for about 40 hours. Referring to FIGS. 5 to 8, clones 1 and 2 were found to have higher lactic acid productivity than the control group, even with glucose uptake rates similar to the glucose uptake rates of the control group. This may be attributed to the relatively low energy consumption for intracellular pH adjustment due to enhanced acid-tolerance of clones 1 and 2, which is not intended to limit the scope of the present disclosure. In FIGS. 5 to 8, clone 1 and clone 2 indicate the results from introducing the pRS426GPD-KanPX vectors including the polynucleotides of SEQ ID Nos. 3 and 4 into the *Saccharomyces cerevisiae* Accession No. KCTC 12415, respectively.

EXAMPLE 2

Acid-Tolerance of IoGAS1 Gene-included Yeast Strains

A vector of clone 1, i.e., a pRS426GPD-KanPX vector (hereinafter, "pRS426GPD-KanPX (SEQ ID NO: 3) vector") including a nucleotide sequence of SEQ ID NO: 3 including an IoGAS1 coding sequence of SEQ ID NO: 2, and an expression vector (hereinafter, "pRS426GPD-KanPX (SEQ ID NO: 2) vector") obtained by inserting only a nucleotide sequence of SEQ ID NO: 2 as a protein-coding DNA sequence taken from the vector of clone 1 into the pRS426GPD-KanPX vector were each introduced into acid-tolerant yeast *S. cerevisiae* CEN.PK2-1 D to investigate changes in the acid tolerance of the yeast.

To construct the pRS426GPD-KanPX (SEQ ID NO: 2) vector, the vector of clone 1 as a template was subjected to a PCR using a primer pair of SEQ ID NOS: 16 and 17 to amplify the coding sequence of the IoGAS1 gene of SEQ ID NO: 2.

The amplified DNA fragments were mixed with the pRS426GPD-KanPX vector cut with XhoI and XbaI restriction enzymes, followed by in-fusion cloning (In-fusion kit, Clontech, catalog #639690) in a kit operation condition set by Clontech. The cloned vector, i.e., the pRS426GPD-KanPX (SEQ ID NO: 2) vector has a sequence of SEQ ID NO: 18.

The cloned vector was introduced into *S. cerevisiae* CEN.PK2-1 D wild-type strain. Five of the resulting colonies were each inoculated onto 1 mL of a SD-URA minimal medium (including 6.7 g of a yeast nitrogen base, 1.92 g of a standard drop-out supplement without uracil, and 20 g of glucose per 1 L of water), and cultured at about 30° C. at about 230 rpm overnight. About 700 uL of the culture medium was inoculated onto 15 mL of a SD-URA minimal medium, and cultured at about 30° C. at about 230 rpm for about 8 hours. One of the culture media with the highest cell concentration was selected and centrifuged at about 3,700 rpm for about 5 minutes to recover the cells, followed by suspended in sterile water to a cell concentration of about 4.5 at $OD_{600}$. About 10 uL of this suspension was inoculated onto about 450 uL of a medium for acid tolerance comparison in a 24-well microplate and cultured for about 20 hours at about 30° C. while being shaken. The medium for acid tolerance comparison was a SD-URA minimal medium of which pH was adjusted with hydrochloric acid or L-lactic acid. Media for comparison of tolerance to hydrochloric acid were prepared to have a pH of 5.5 (not adjusted), a pH of 3.00, a pH of 2.85, a pH of 2.70, a pH of 2.55, a pH of 2.40, a pH of 2.25, and a pH of 2.10, respectively, and then sterilized using a filter. Media for comparison of tolerance to lactic acid were prepared to have a pH of 5.5 (not adjusted), a pH of 3.00, a pH of 2.90, a pH of 2.80, a pH of 2.70, a pH of 2.60, a pH of 2.50, and a pH of 2.40, respectively, and were then sterilized using a filter. During the culture process, the shaking rates of the media were automatically controlled, the culture incubator was maintained at a humidity of 95% or higher, and oxygen concentration in the incubator was maintained at an atmospheric level for aerobic growth. After the culture process, about 100 uL of each of the cell culture media was mixed with about 900 uL of a 10 mM Tris-HCl (pH 8.0) buffer, and absorbance at an OD of 600 nm was read to measure a cell concentration in the cell culture medium.

Figure 9:
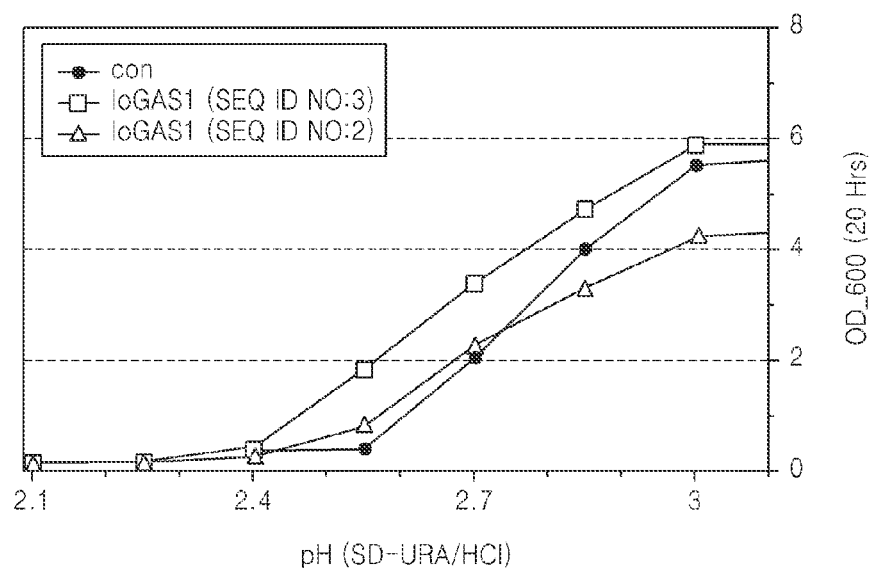
FIG. 9 is a graph of displaying the growth of different recombinant yeast cells at different pH levels in acidic media comprising HCl.

FIG. 9 is a graph of growth of different recombinant yeast cells in HCl-included acidic media at different pH levels.

Figure 10:
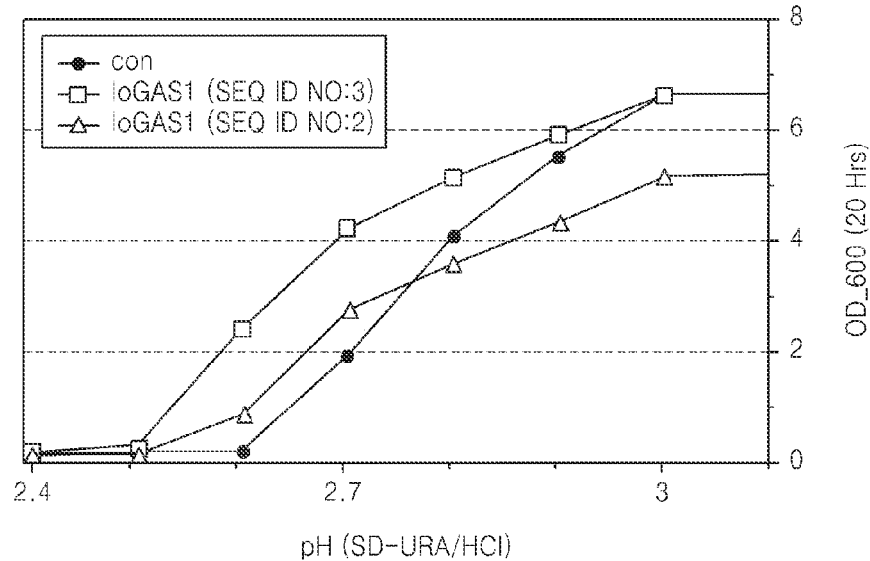
FIG. 10 is a graph displaying the growth of the recombinant yeast cells in lactic acid-included acidic media at different pH levels.

FIG. 10 is a graph of growth of the recombinant yeast cells in lactic acid-included acidic media at different pH levels.

Figure 11:
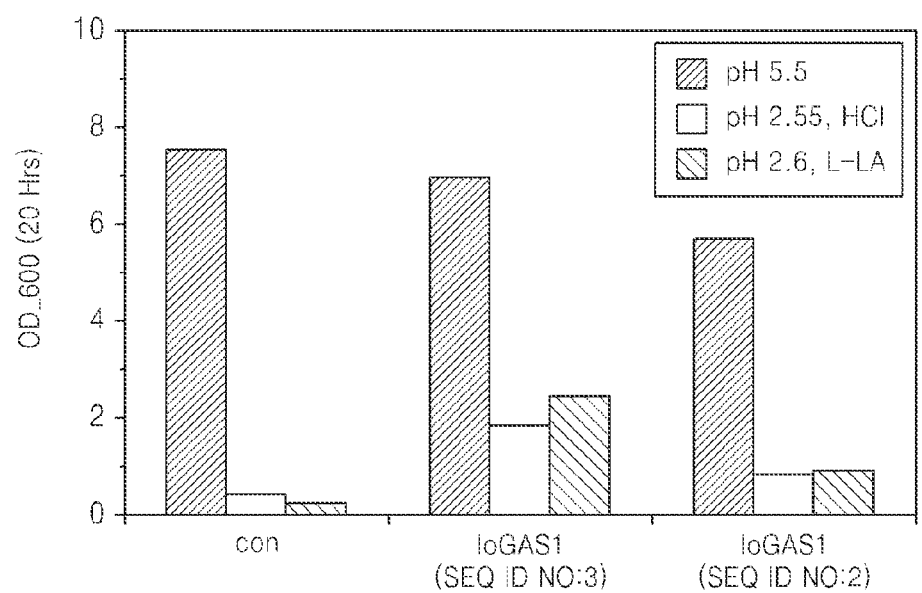
FIG. 11 is a graph displaying the growth of the recombinant yeast cells cultured in different acidic media for about 20 hours.

FIG. 11 is a graph of growth of the recombinant yeast cells for about 20 hours in different acidic media at a pH of 5.5 (not adjusted), a pH of 2.55 adjusted with HCl, and a pH of 2.6 adjusted with lactic acid, respectively.

Referring to FIGS. 9 to 11, "IoGAS1 (SEQ ID NO: 3)" and "IoGAS1 (SEQ ID NO: 2)" indicate the *S. cerevisiae* CEN.PK2-1 D strains into which the pRS426GPD-KanPX (SEQ ID NO: 3) vector and pRS426GPD-KanPX (SEQ ID NO: 2) vector were introduced, respectively.

Referring to FIG. 9, the *S. cerevisiae* CEN.PK2-1 D strains into which the pRS426GPD-KanPX (SEQ ID NO: 3) vector and pRS426GPD-KanPX (SEQ ID NO: 2) vector were introduced, respectively were found to have grown more in the HCl-included acidic media at a low pH, and particularly, at a pH of about 2.7 or less, than the control group.

Referring to FIG. 10, the *S. cerevisiae* CEN.PK2-1D strains into which the pRS426GPD-KanPX (SEQ ID NO: 3) vector and pRS426GPD-KanPX (SEQ ID NO: 2) vector were introduced, respectively were also found to have grown more in the lactic acid-included acidic media at a low pH, and particularly, at a pH of about 2.7 or less, than the control group.

The results indicate that, the stronger the acidity was, the more the yeast strains of Example 2 prepared to include the IoGAS1 genes were grown compared to the control group, indicating that they had an unexpected tolerance to acid, irrespective of the production of organic acid or types of organic acids produced by the yeast.

Referring to FIGS. 9 to 11, the *S. cerevisiae* CEN.PK2-1 D yeast strains that were cultured in the media adjusted to an acidic pH so that the IoGAS1 gene introduced thereinto was expressed were found to have enhanced tolerance to acid, i.e., to both HCl and L-lactic acid.

As described in the above examples, the yeast strains including the pRS426GPD-KanPX (SEQ ID NO: 3) vector or pRS426GPD-KanPX (SEQ ID NO: 2) vector may grow more than the control group under acidic conditions, with unexpected tolerance to acid. The yeast cells including the IoGAS1 gene may grow even at an acidic pH at which normal yeast cells have a markedly suppressed growth rate, for example, even at a pH of 2.1 to 7.5, a pH of 2.1 to 2.7, a pH of 2.1 to 2.6, a pH of 2.1 to 2.5, a pH of 2.1 to 2.4, a pH of 2.1 to 2.3, a pH of 2.1 to 2.2, a pH of 2.2 to 2.75, a pH of 2.2 to 2.7, a pH of 2.2 to 2.6, a pH of 2.2 to 2.5, a pH of 2.2 to 2.4, a pH of 2.2 to 2.3, a pH of 2.3 to 2.75, a pH of 2.3 to 2.70, a pH of 2.3 to 2.6, a pH of 2.3 to 2.5, a pH of 2.3 to 2.4, a pH of 2.4 to 2.75, a pH of 2.4 to 2.70, a pH of 2.4 to 2.6, a pH of 2.4 to 2.5, a pH of 2.5 to 2.75, a pH of 2.5 to 2.70, or a pH of 2.5 to 2.6.

As described above, according to the one or more of the above embodiments of the present invention, a polypeptide having an amino acid sequence with a sequence identity of about 65% or greater, for example about 95% or greater with respect to SEQ ID NO: 1 may confer acid tolerance to a yeast. The polynucleotide encoding the polypeptide is able to confer acid tolerance on a yeast. A yeast cell including an increased amount of the polypeptide may have tolerance to acid. A product may be produced by using the acid-tolerant yeast cell by an efficient method.

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A genetically modified yeast cell comprising a gene encoding a polypeptide comprising the amino acid sequence of SEQ ID NO: 1,
   wherein the gene encoding the polypeptide comprising the amino acid sequence of SEQ ID NO: 1 is heterologous to the yeast cell.

2. The yeast cell of claim 1, wherein the yeast cell is selected from the group consisting of the genus *Issatchenkia*, the genus *Kluyveromyces*, the genus *Pichia*, the genus *Saccharomyces*, the genus *Zygosaccharomyces*, and the genus *Schizosaccharomyces*.

3. The yeast cell of claim 1, wherein the yeast is more tolerant of an organic acid, an inorganic acid, or a combination thereof, as compared to a corresponding yeast cell not comprising the gene encoding a polypeptide comprising the amino acid sequence of SEQ ID NO: 1.

4. The yeast cell of claim 3, wherein the yeast cell is more tolerant of an acetic acid, a lactic acid, a propionic acid, a 3-hydroxy propionic acid, a butyric acid, a 4-hydroxy butyric acid, a succinic acid, a fumaric acid, a malic acid, an oxalic acid, an adipic acid, a hydrochloric acid, a sulfuric acid, or a combination thereof.

5. The yeast cell of claim 1, wherein the yeast cell has a higher growth rate at a pH of 2.0 to 3.0 as compared to a corresponding yeast cell not comprising the gene encoding a polypeptide comprising the amino acid sequence of SEQ ID NO.: 1.

6. The yeast cell of claim 1, wherein the yeast cell further comprises a gene encoding lactate dehydrogenase that converts pyruvate to lactate.

7. The yeast cell of claim 1, wherein a gene encoding a polypeptide for converting pyruvate into acetaldehyde, a gene encoding a polypeptide for converting lactate into pyruvate, a gene encoding a polypeptide for converting dihydroxyacetone phosphate (DHAP) into glycerol-3-phosphate (G3P), or a combination thereof is inactivated or is attenuated in the yeast cell.

8. The yeast cell of claim 1, wherein the yeast cell is the yeast cell deposited with Accession No. KCTC 12415 BP comprising a gene encoding a polypeptide having the amino acid sequence of SEQ ID NO: 1.

9. A method of producing a product using a yeast cell, the method comprising:
   culturing the yeast cell of claim 1 in a medium, whereby the yeast cell generates a product; and
   isolating the product from the culture,
   wherein the product is an organic acid selected from the group consisting of an acetic acid, a lactic acid, a propionic acid, a 3-hydroxy propionic acid, a butyric acid, a 4-hydroxy butyric acid, a succinic acid, a fumaric acid, a malic acid, an oxalic acid, an adipic acid, and a combination thereof.

10. The method of claim 9, wherein the culturing is performed under acidic conditions for the entire time period of culturing or part of the time period of culturing.

11. The method of claim 10, wherein the acidic conditions comprise a pH of 2.0 to 4.0.

12. The method of claim 9, wherein the isolating step comprises isolating a free acid from the culture.

13. The method of claim 9, wherein the product comprises lactic acid.

14. A method of producing a genetically modified yeast cell, the method comprising transforming a yeast cell with a polynucleotide comprising a gene encoding a polypeptide comprising the amino acid sequence of SEQ ID NO: 1, wherein the gene encoding the polypeptide comprising the amino acid sequence of SEQ ID NO: 1 is heterologous to the yeast cell.

15. A genetically modified yeast cell comprising a vector comprising a gene encoding a polypeptide comprising the amino acid sequence of SEQ ID NO: 1, wherein the gene encoding the polypeptide comprising the amino acid sequence of SEQ ID NO: 1 is heterologous to the yeast cell.

16. The genetically modified yeast cell of claim 15, wherein the vector is introduced into the cell by transformation.

17. The genetically modified yeast cell of claim 1, wherein the gene encoding the polypeptide comprising the amino acid sequence of SEQ ID NO: 1 is introduced into the cell by transformation.

18. The genetically modified yeast cell of claim 1, wherein the genetically modified yeast cell exhibits increased growth rate when cultured under acidic conditions as compared to a corresponding yeast cell not comprising the gene encoding a polypeptide comprising the amino acid sequence of SEQ ID NO: 1.

* * * * *